(12) United States Patent
Ensinger et al.

(10) Patent No.: US 6,605,600 B1
(45) Date of Patent: Aug. 12, 2003

(54) ADENOSINE RECEPTOR ANTAGONISTS AND METHODS OF MAKING AND USING THE SAME

(75) Inventors: Carol L. Ensinger, Chelmsford, MA (US); James E. Dowling, Scituate, MA (US); Russell C. Petter, Stow, MA (US); Gnanasambandam Kumaravel, Westford, MA (US)

(73) Assignee: Biogen, Incorporated, Cambridge, MA (US)

( * ) Notice: Subject to any disclaimer, the term of this patent is extended or adjusted under 35 U.S.C. 154(b) by 0 days.

(21) Appl. No.: 09/711,554

(22) Filed: Nov. 13, 2000

Related U.S. Application Data
(60) Provisional application No. 60/165,283, filed on Nov. 12, 1999.

(51) Int. Cl.⁷ .................. C07D 473/06; C07D 473/20; C07D 473/22; C07D 519/00; A61K 31/522
(52) U.S. Cl. ................. 514/81; 514/263.2; 514/263.22; 514/263.23; 514/263.34; 514/263.35; 514/263.36; 544/268; 544/270; 544/271; 544/272; 544/273; 544/267
(58) Field of Search ................. 544/268, 270, 544/271, 272, 273, 267, 244; 514/263, 265, 81, 263.23, 263.22, 263.34, 263.35

(56) References Cited

U.S. PATENT DOCUMENTS
5,270,316 A 12/1993 Suzuki et al.

(List continued on next page.)

FOREIGN PATENT DOCUMENTS
DE 3843117 A1 6/1990

(List continued on next page.)

OTHER PUBLICATIONS
J. Shimada et al. "8–Polycycloalkyl–1, 3–dipropylxanthines as Potent Selective Antagonists for A1–Adenosine Receptors", J. Med. Chem., vol. 35, No. 5, 1992, pp. 924–930.

(List continued on next page.)

*Primary Examiner*—Mark L. Berch
(74) *Attorney, Agent, or Firm*—Fish & Neave; James F. Haley, Jr.; Kristin M. Joslyn

(57) ABSTRACT

The invention is based on the discovery that compounds of Formula I are unexpectedly highly potent and selective inhibitors of the adenosine $A_1$ receptor. Adenosine $A_1$ antagonists can be useful in the prevention and/or treatment of numerous diseases, including cardiac and circulatory disorders, degenerative disorders of the central nervous system, respiratory disorders, and many diseases for which diuretic treatment is suitable.

In one embodiment, the invention features a compound of formula I:

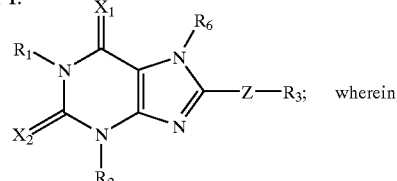

$R_3$ is an optionally substituted group selected from:

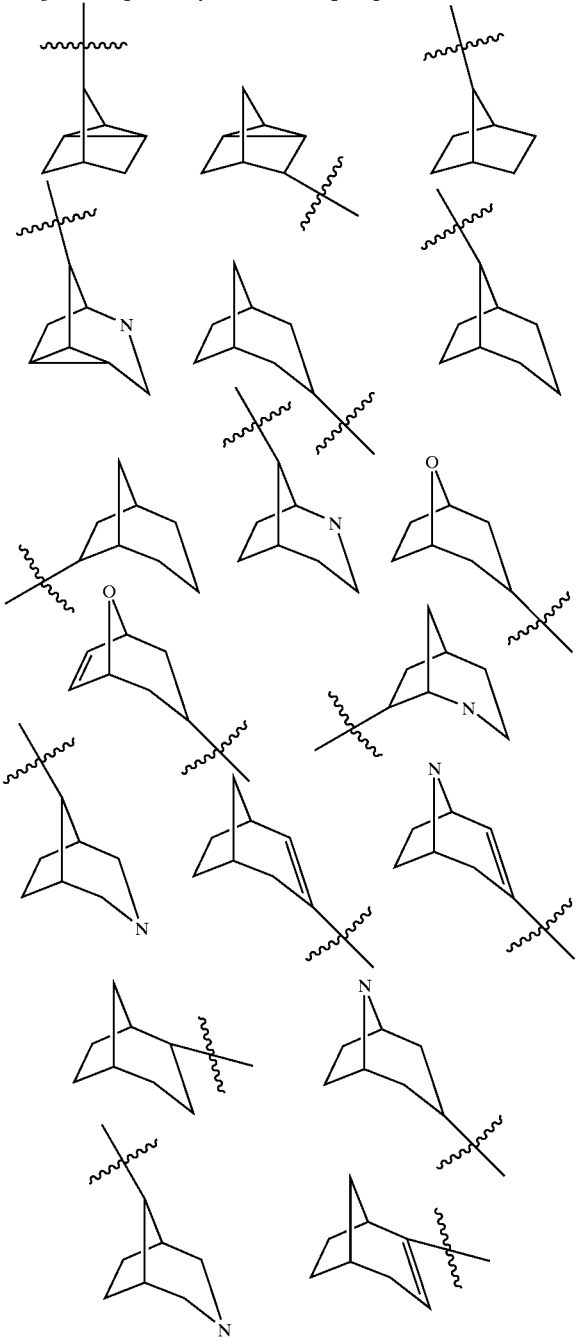

and wherein $X_1$, $X_2$, $Z$, $R_1$, $R_2$, and $R_6$ are as described in the specification.

29 Claims, 6 Drawing Sheets

U.S. PATENT DOCUMENTS

| | | |
|---|---|---|
| 5,290,782 A | 3/1994 | Suzuki et al. |
| 5,525,607 A | 6/1996 | Suzuki et al. |
| 5,532,368 A | 7/1996 | Kufner-Muhl et al. |
| 5,641,784 A | 6/1997 | Kufner-Muhl et al. |

FOREIGN PATENT DOCUMENTS

| | | |
|---|---|---|
| DE | 4019892 A1 | 1/1992 |
| DE | 19816857 A1 | 10/1999 |
| EP | 0415456 A2 | 3/1991 |
| EP | 0423805 A3 | 4/1991 |
| EP | 0501379 A2 | 9/1992 |
| EP | 0541120 A2 | 5/1993 |
| EP | 0556778 A2 | 8/1993 |
| EP | 0560354 A1 | 9/1993 |
| EP | 0619316 A1 | 10/1994 |
| WO | WO94/03456 | 2/1994 |
| WO | WO94/16702 | 8/1994 |
| WO | WO98/57644 | 12/1998 |
| WO | WO98/57645 | 12/1998 |
| WO | WO00/01388 | 1/2000 |

OTHER PUBLICATIONS

Patent Abstracts of Japan, vol. 017, No. 063, Feb. 8, 1993 for JP 04 270222 A, Sep. 25, 1992.

Patent Abstracts of Japan, vol. 017, No. 200, Apr. 20, 1993 for JP 04 346986 A, Dec. 2, 1992.

Suzuki et al., "Adenosine $A_1$ Antagognists. 2.[554] Structure–Activity Relationships on Diuretic Activities and Protective Effects against Acute Renal Failure"; J. Med. Chem. 1992, 35, 3066–30 75.

ADENOSINE RECEPTOR ANTAGONISTS AND METHODS OF MAKING AND USING THE SAME

CROSS REFERENCE TO RELATED APPLICATIONS

This application claims priority from U.S. Provisional Application Serial No. 60/165,283, filed on Nov. 12, 1999.

BACKGROUND OF THE INVENTION

The invention relates to antagonists of adenosine receptors and methods of making and using the same in the treatment of diseases.

Adenosine is an intracellular and extracellular messenger generated by all cells in the body. It is also generated extracellularly by enzymatic conversion. Adenosine binds to and activates seven transmembrane g-protein coupled receptors, eliciting a variety of physiological responses. Adenosine itself, substances that mimic the actions of adenosine (agonists), and substances that antagonize its actions have important clinical applications. Adenosine receptors are divided into four known subtypes (i.e., $A_1$, $A_{2a}$, $A_{2b}$, and $A_3$). These subtypes elicit unique and sometimes opposing effects. Activation of the adenosine $A_1$ receptor, for example, elicits an increase in renal vascular resistance while activation of the adenosine $A_{2a}$ receptor elicits a decrease in renal vascular resistance.

In most organ systems, periods of metabolic stress result in significant increases in the concentration of adenosine in the tissue. The heart, for instance, produces and releases adenosine to mediate adaptive responses to stress, such as reductions in heart rate and coronary vasodilatation. Likewise, adenosine concentrations in kidneys increase in response to hypoxia, metabolic stress and many nephrotoxic substances. The kidneys also produce adenosine constitutively. The kidneys adjust the amount of constitutively produced adenosine in order to regulate glomerular filtration and electrolyte reabsorption. Regarding control of glomerular filtration, activation of $A_1$ receptors leads to constriction of afferent arterioles while activation of $A_{2a}$ receptors leads to dilatation of efferent arterioles. Activation of $A_{2a}$ receptors may also exert vasodilatory effects on the afferent arteriole. Overall, the effect of activation of these glomerular adenosine receptors is to reduce glomerular filtration rate. In addition, $A_1$ adenosine receptors are located in the proximal tubule and distal tubular sites. Activation of these receptors stimulates sodium reabsorption from the tubular lumen. Accordingly, blocking the effects of adenosine on these receptors will produce a rise in glomerular filtration rate and an increase in sodium excretion.

SUMMARY OF THE INVENTION

The invention is based on the discovery that compounds of Formula I are unexpectedly highly potent and selective inhibitors of particular subtypes of adenosine receptors. Adenosine antagonists can be useful in the prevention and/or treatment of numerous diseases, including cardiac and circulatory disorders, degenerative disorders of the central nervous system, respiratory disorders, and many diseases for which diuretic treatment is suitable.

In one embodiment, the invention features a compound of formula (I):

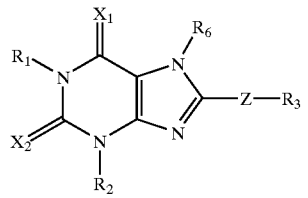

(I)

where $R_1$ and $R_2$ are independently chosen from: (a) hydrogen; (b) alkyl, alkenyl of not less than 3 carbons, or alkynyl of not less than 3 carbons; wherein the alkyl, alkenyl, or alkynyl is either unsubstituted or functionalized with one or two substituents selected from the group consisting of hydroxy, alkoxy, amino, alkylamino, dialkylamino, heterocyclyl, acylamino, alkylsulfonylamino, and heterocyclylcarbonylamino; and (c) aryl and substituted aryl.

$R_3$ is a bicyclic or tricyclic group chosen from:

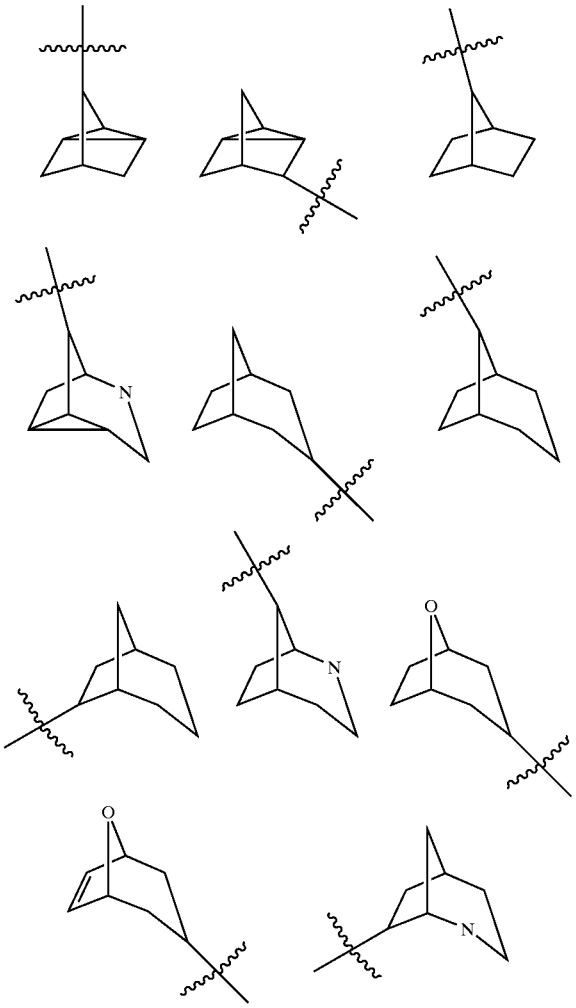

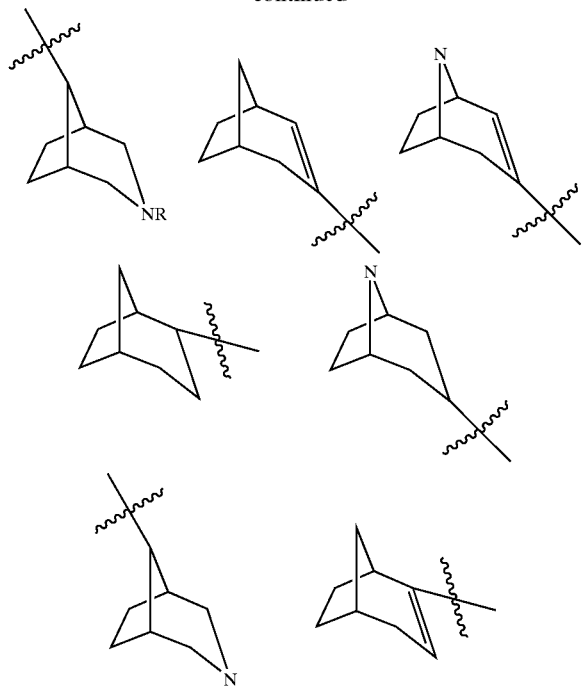

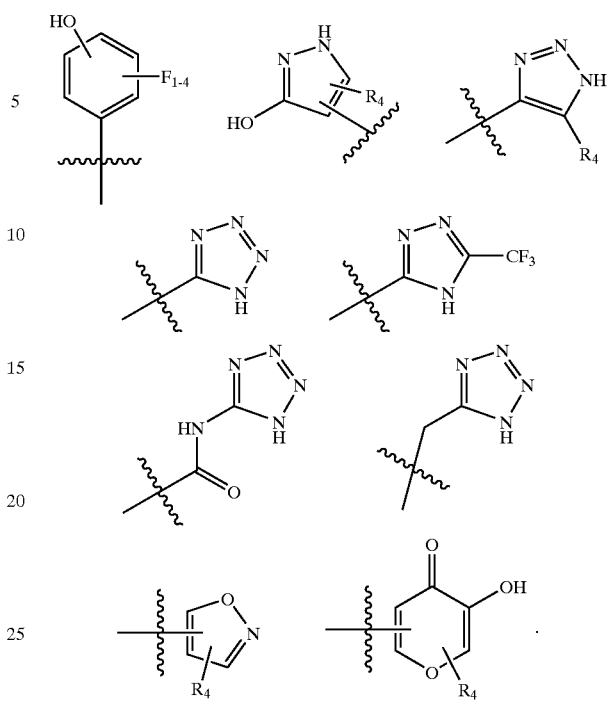

where the bicyclic or tricyclic group can be unsubstituted or can be functionalized with one or more (e.g., one, two, three, or more) substituents chosen from: (a) alkyl, alkenyl, and alkynyl; wherein the alkyl, alkenyl, and alkynyl are either unsubstituted or functionalized with one or more substituents selected from the group consisting of alkoxy, alkoxycarbonyl, alkoxycarbonylaminoalkylamino, aralkoxycarbonyl, —R5, dialkylamino, heterocyclylalkylamino, hydroxy, substituted arylsulfonylaminoalkylamino, and substituted heterocyclylaminoalkylamino; (b) acylaminoalkylamino, alkenylamino, alkoxycarbonyl, alkoxycarbonyl, alkoxycarbonylalkylamino, alkoxycarbonylaminoacyloxy, alkoxycarbonylaminoalkylamino, alkylamino, amino, aminoacyloxy, carbonyl, —R5, R5-alkoxy, R5-alkylamino, dialkylaminoalkylamino, heterocyclyl, heterocyclylalkylamino, hydroxy, phosphate, substituted arylsulfonylaminoalkylamino, substituted heterocyclyl, and substituted heterocyclylaminoalkylamino.

$R_4$ is chosen from —H, —$C_{1-4}$-alkyl, —$C_{1-4}$-alkyl-$CO_2H$, and phenyl; and can be unsubstituted or can be functionalized with one or more substituents chosen from halogen, —OH, —OMe, —$NH_2$, —$NO_2$ and benzyl, optionally substituted with one, two, or three groups selected from halogen, —OH, —OMe, —$NH_2$, and —$NO_2$.

$R_5$ is chosen from —$CH_2COOH$, —$C(CF_3)_2OH$, —$CONHNHSO_2CF_3$, —$CONHOR_4$, —$CONHSO_2R_4$, —$CONHSO_2NHR_4$, —$C(OH)R_4PO_3H_2$, —$NHCOCF_3$, —$NHCONHSO_2R_4$, —$NHPO_3H_2$, —$NHSO_2R_4$, —$NHSO_2NHCOR_4$, —$OPO_3H_2$, —$OSO_3H$, —$PO(OH)R_4$, —$PO_3H_2$, —$SO_3H$, —$SO_2NHR_4$, —$SO_3NHCOR_4$, —$SO_3NHCONHCO_2R_4$, and the following:

$X_1$ and $X_2$ are chosen, independently, from oxygen (O) and sulfur (S).

Z is chosen from a single bond, —O—, —$(CH_2)_{1-3}$—, —$O(CH_2)_{1-2}$—, $CH_2OCH_2$—, —$(CH_2)_{1-2}O$—, and —$CH_2CH=CH$—.

$R_6$ is chosen from hydrogen, alkyl, acyl, alkylsufonyl, aralkyl, substituted aralkyl, substituted alkyl, and heterocyclyl.

$R_6$ is preferably hydrogen. However, when $R_6$ is methyl or another non-hydrogen substituent, the compounds can be highly selective for inhibition of adenosine $A_{2a}$ receptors.

In certain embodiments, $R_1$ and $R_2$ can be the same or different alkyl groups. For example, one or both can be n-propyl.

In some embodiments, Z is a single bond.

In one embodiment, $R_3$ is chosen from the following bicyclic and tricyclic structures:

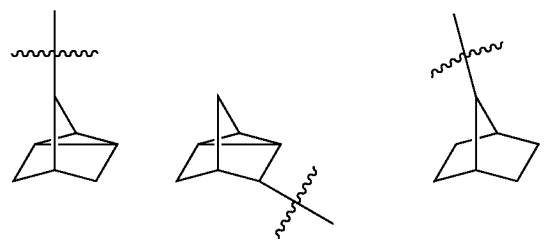

and is functionalized with one or more substituents chosen from carbonyl, hydroxy, alkenyl, alkenyloxy, hydroxyalkyl, carboxy, carboxyalkenyl, carboxyalkyl, aminoacyloxy, carboxyalkoxy, dialkylaminoalkenyl, and dialkylaminoalkyl.

In another embodiment, $R_3$ is:

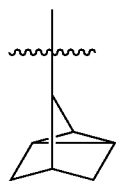

and is functionalized with one or more substituents chosen from carbonyl, hydroxy, alkenyl, carboxyalkenyl, hydroxyalkyl, dialkylaminoalkenyl, and dialkylaminoalkyl. Thus, for example, the compound can be 8-(5-Hydroxy-tricyclo[2.2.1.0$^{2,6}$]hept-3-yl)-1,3-dipropyl-3,7-dihydro-purine-2,6-dione; 8-(5-Hydroxymethyl-tricyclo[2.2.1.0$^{2,6}$]hept-3-yl)-1,3-dipropyl-3,7-dihydro-purine-2,6-dione; 8-[5-(3-Dimethylaminopropylidene)-tricyclo[2.2.1.0$^{2,6}$]hept-3-yl]-1,3-dipropyl-3,7-dihydro-purine-2,6-dione; or 8-[5-(3-Dimethylaminopropyl)-tricyclo[2.2.1.0$^{2,6}$]hept-3-yl]-1,3-dipropyl-3,7-dihydro-purine-2,6-dione.

In still another embodiment, $R_3$ is:

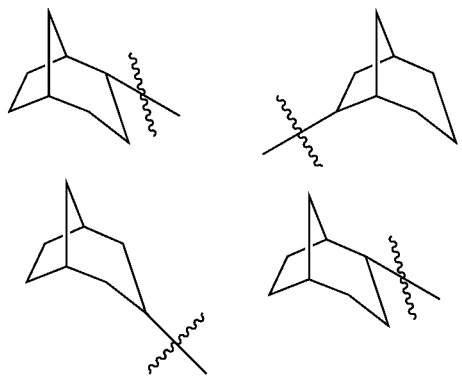

and is functionalized with one or more substituents chosen from hydroxy, carbonyl, alkyl, —$R_5$, $R_5$-alkyl, dialkylaminoalkylamino, alkoxycarbonylalkylamino, $R_5$-alkylamino, heterocyclyl, alkenylamino, amino, alkylamino, heterocyclylalkylamino, acylaminoalkylamino, phosphate, heterocyclylaminoalkylamino, and heterocyclylaminoalkylaminoalkyl.

In yet another embodiment, $R_3$ is:

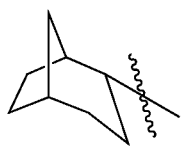

and is functionalized with one or more substituents chosen from hydroxy, —$R_5$, $R_5$-alkyl, and hydroxyalkyl. Thus, for example, the compound can be 4-(2,6-Dioxo-1,3-dipropyl-2,3,6,7-tetrahydro-1H-purin-8-yl)-bicyclo[3.2.1]octane-1-carboxylic acid.

In another embodiment, $R_3$ is:

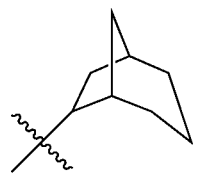

and is functionalized with one or more substituents chosen from alkyl, hydroxy, carbonyl, —$R_5$, and $R_5$-alkyl. Thus, for example, the compound can be 8-(4-Hydroxy-bicyclo[3.2.1]oct-6-yl)-1,3-dipropyl-3,7-dihydro-purine-2,6-dione; or 8-(4-Oxo-bicyclo[3.2.1]oct-6-yl)-1,3-dipropyl-3,7-dihydro-purine-2,6-dione.

In still another embodiment, $R_3$ is:

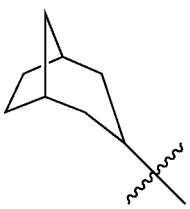

and is functionalized with one or more substituents chosen from carbonyl, hydroxy, dialkylaminoalkylamino, —R5, and substituted heterocyclylaminoalkylaminoalkyl. Thus, for example, the compound can be 8-[8-(2-Dimethylaminoethylamino)-bicyclo[3.2.1]oct-3-yl]-1,3-dipropyl-3,7-dihydro-purine-2,6-dione; or 8-(8-Hydroxy-bicyclo[3.2.1]oct-3-yl)-1,3-dipropyl-3,7-dihydro-purine-2,6-dione.

In yet another embodiment, $R_3$ is:

and is functionalized with one or more substituents chosen from carbonyl, hydroxy, and —R5. Thus, for example, the compound can be 8-(3-Hydroxy-bicyclo[3.2.1]oct-8-yl)-1,3-dipropyl-3,7-dihydro-purine-2,6-dione.

In yet another embodiment, $R_3$ is selected from bicycles:

and is functionalized with one or more substituents chosen from hydroxyalkyl, hydroxy, and alkoxycarbonyl. Thus, for example, the compound can be 8-(8-Oxa-bicyclo[3.2.1]oct-6-en-3-yl)-1,3-dipropyl-3,7-dihydro-purine-2,6-dione.

In yet another embodiment, $R_3$ is:

and is functionalized with one or more substituents chosen from carbonyl, aralkyloxycarbonylalkyl, and alkoxycarbonylalkyl. Thus, for example, the compound can be 8-(2-Oxo-3-aza-bicyclo[3.2.1]oct-8-yl)-1,3-dipropyl-3,7-dihydro-purine-2,6-dione.

The compound can be, for example, in a form of an achiral compound, a racemate, an optically active compound, a pure diastereomer, a mixture of diastereomers, or a pharmacologically acceptable addition salt.

The compounds of this invention can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

The invention also features a medicament composition including any of the above compounds, alone or in a combination, together with a suitable excipient.

The invention also features a method of treating a subject suffering from a condition characterized by an elevated adenosine concentration and/or increased sensitivity to adenosine and/or elevated adenosine receptor number or coupling efficiency. The method includes the step of administering to the subject an amount of any of the above compounds to be effective as an adenosine $A_1$ receptor antagonist. The condition can be, for example, a cardiac and circulatory disorder, a degenerative disorder of the central nervous system, a respiratory disorder, a disease for which diuretic treatment is indicated, hypertension, Parkinson's disease, depression, traumatic brain damage, post-stroke neurological deficit, respiratory depression, neonatal brain trauma, dyslexia, hyperactivity, cystic fibrosis, cirrhotic ascites, neonatal apnea, renal failure, diabetes, asthma, an edematous condition, congestive heart failure, or renal dysfunction associated with diuretic use in congestive heart failure.

The invention also features a method of making 8-substituted xanthines. The method includes the steps of obtaining a N7,C8-dihydroxanthine, protecting the N7 position of the xanthine (e.g., as a THP or BOM ether); deprotonating the C8 position with strong base (such as lithium di-isopropyl amide or n-butyl lithium) to generate an anion; trapping the anion with a carboxyl, carbonyl, aldehyde, or ketone compound; and deprotecting the protected N7 position to obtain an 8-substituted xanthine.

As used herein, an "alkyl" group is a saturated aliphatic hydrocarbon group. An alkyl group can be straight or branched, and can have, for example, from 1 to 6 carbon atoms in a chain. Examples of straight chain alkyl groups include, but are not limited to, ethyl and butyl. Examples of branched alkyl groups include, but are not limited to, isopropyl and t-butyl.

An "alkenyl" group is an aliphatic carbon group that has at least one double bond. An alkenyl group can be straight or branched, and can have, for example, from 3 to 6 carbon atoms in a chain and 1 or 2 double bonds. Examples of alkenyl groups include, but are not limited to, allyl and isoprenyl.

An "alkynyl" group is an aliphatic carbon group that has at least one triple bond. An alkynyl group can be straight or branched, and can have, for example, from 3 to 6 carbon atoms in a chain and 1 to 2 triple bonds. Examples of alkynyl groups include, but are not limited to, propargyl and butynyl.

An "aryl" group is a phenyl or naphthyl group, or a derivative thereof. A "substituted aryl" group is an aryl group that is substituted with one or more substituents such as alkyl, alkoxy, amino, nitro, carboxy, carboalkoxy, cyano, alkylamino, dialkylamino, halo, hydroxy, hydroxyalkyl, mercaptyl, alkylmercaptyl, trihaloalkyl, carboxyalkyl, sulfoxy, or carbamoyl.

An "aralkyl" group is an alkyl group that is substituted with an aryl group. An example of an aralkyl group is benzyl.

A "cycloalkyl" group is an aliphatic ring of, for example, 3 to 8 carbon atoms. Examples of cycloalkyl groups include cyclopropyl and cyclohexyl.

An "acyl" group is a straight or branched alkyl-C(=O)— group or a formyl group. Examples of acyl groups include alkanoyl groups (e.g., having from 1 to 6 carbon atoms in the alkyl group). Acetyl and pivaloyl are examples of acyl groups. Acyl groups may be substituted or unsubstituted.

A "carbamoyl" group is a group having the structure $H_2N-CO_2-$. "Alkylcarbamoyl" and "dialkylcarbamoyl" refer to carbamoyl groups in which the nitrogen has one or two alkyl groups attached in place of the hydrogens, respectively. By analogy, "arylcarbamoyl" and "arylalkylcarbamoyl" groups include an aryl group in place of one of the hydrogens and, in the latter case, an alkyl group in place of the second hydrogen.

A "carboxyl" group is a —COOH group.

An "alkoxy" group is an alkyl-O— group in which "alkyl" is as previously described.

An "alkoxyalkyl" group is an alkyl group as previously described, with a hydrogen replaced by an alkoxy group, as previously described.

A "halogen" or "halo" group is fluorine, chlorine, bromine or iodine.

A "heterocyclyl" group is a 5 to about 10 membered ring structure, in which one or more of the atoms in the ring is an element other than carbon, e.g., N, O, S. A heterocyclyl group can be aromatic or non-aromatic, i.e., can be saturated, or can be partially or fully unsaturated. Examples of heterocyclyl groups include pyridyl, imidazolyl, furanyl, thienyl, thiazolyl, tetrahydrofuranyl, tetrahydropyranyl, morpholinyl, thiomorpholinyl, indolyl, indolinyl, isoindolinyl, piperidinyl, pyrimidinyl, piperazinyl, isoxazolyl, isoxazolidinyl, tetrazolyl, and benzimidazolyl.

A "substituted heterocyclyl" group is a heterocyclyl group wherein one or more hydrogens are replaced by substituents such as alkoxy, alkylamino, dialkylamino, carbalkoxy, carbamoyl, cyano, halo, trihalomethyl, hydroxy, carbonyl, thiocarbonyl, hydroxyalkyl or nitro.

A "hydroxyalkyl" means an alkyl group substituted by a hydroxy group.

A "sulfamoyl" group has the structure —$S(O)_2NH_2$. "Alkylsulfamoyl" and "dialkylsulfamoyl" refer to sulfamoyl groups in which the nitrogen has one or two alkyl groups attached in place of the hydrogens, respectively. By analogy, "arylsulfamoyl" and "arylalkylsulfamoyl" groups include an aryl group in place of one of the hydrogens and, in the latter case, an alkyl group in place of the second hydrogen.

An "antagonist" is a molecule that binds to a receptor without activating the receptor. It competes with the endogenous ligand for this binding site and, thus, reduces the ability of the endogenous ligand to stimulate the receptor.

In the context of the present invention, a "selective antagonist" is an antagonist that binds to a specific subtype of adenosine receptor with higher affinity than to other subtypes. The antagonists of the invention can, for example, have high affinity for $A_1$ receptors or for $A_{2a}$ receptors and are selective, having (a) nanomolar binding affinity for one of these two subtypes and (b) at least 10 times, more preferably 50 times, and most preferably at least 100 times, greater affinity for one subtype than for the other.

The invention provides numerous advantages. The compounds are easily manufactured from readily available starting materials, in a relatively small number of steps. The compounds have a number of variable regions, allowing for systematic optimization. As $A_1$-specific antagonists, the compounds have broad medicinal utility. Since the compounds are highly potent and specific $A_1$ antagonists, they can (1) be used in low doses to minimize the likelihood of side effects and (2) be incorporated into numerous dosage forms including, but not limited to, pills, tablets, capsules, aerosols, suppositories, liquid formulations for ingestion or injection, dietary supplements, or topical preparations. In addition to medical applications, the antagonist compound can be used in the treatment of livestock and pet animals.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Other features and advantages of the invention will be apparent from the following detailed description, and from the claims.

DESCRIPTION OF THE PREFERRED EMBODIMENTS

Figure 1A:
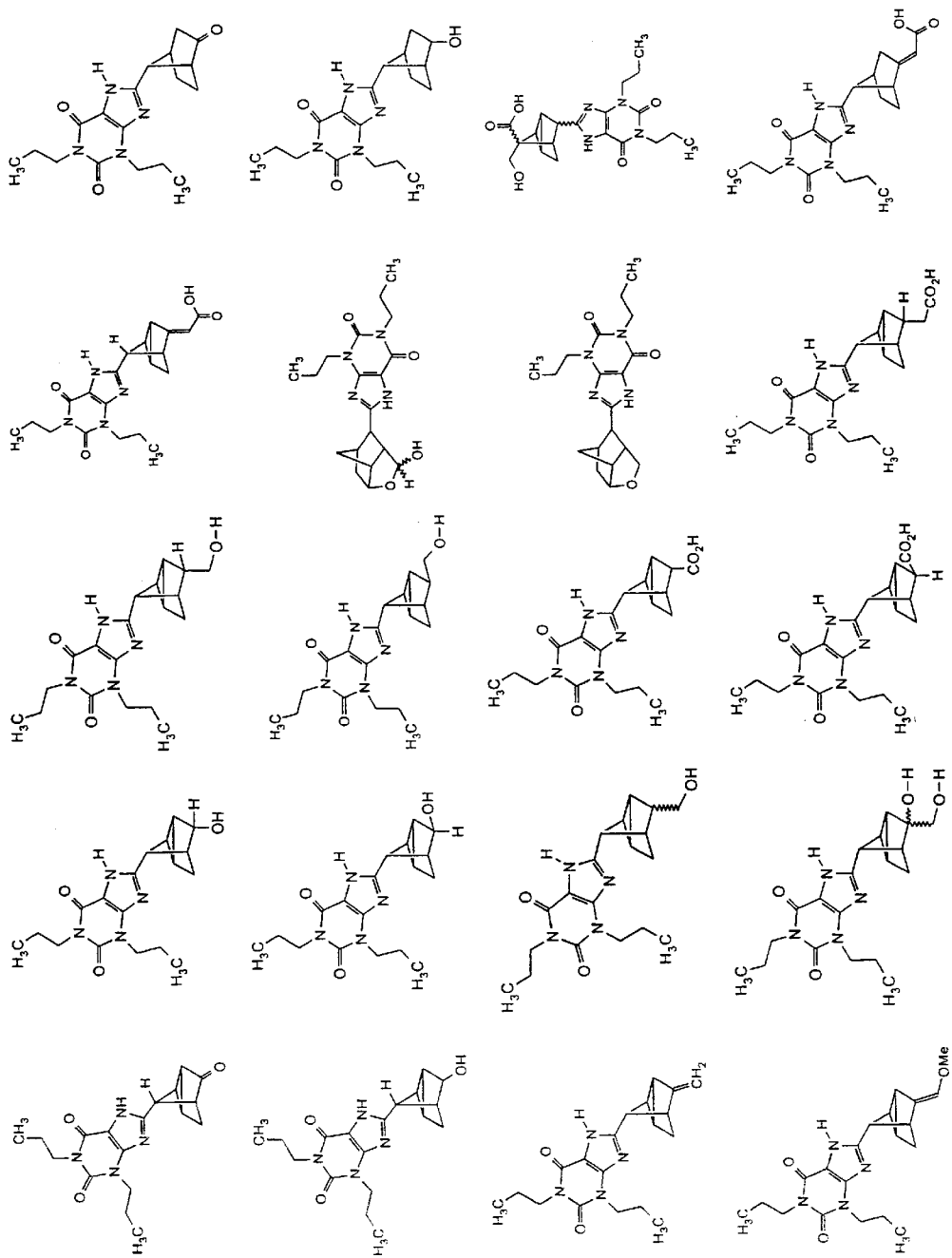
FIG. 1 is a series of illustrations of adenosine $A_1$ antagonists.

In general, the invention features highly potent and selective antagonists of the adenosine $A_1$ receptor. Selective antagonists of the adenosine $A_{2a}$ receptor are also disclosed.

Synthesis of the Adenosine Antagonist Compounds

The compounds of the invention may be prepared by a number of known methods. In general, xanthines can be obtained by the reaction of 1,3-disubstituted-5,6-diaminouracils with aldehydes or carboxylic acids or carboxylic acid chlorides, followed by ring closure. Alternatively, 1,3-disubstituted-6-amino-5-nitrosouracils can be condensed with aldehydes to afford the desired xanthines.

1,3-Disubstituted-5,6-diaminouracils can be prepared by treating the corresponding symmetrically or unsymmetrically substituted urea with cyanoacetic acid, followed by nitrosation and reduction (see, e.g., *J. Org. Chem.* 16, 1879, 1951; *Can J. Chem.* 46, 3413, 1968). Alternatively, unsymmetrically substituted xanthines can be accessed via the method of Mueller (*J. Med. Chem.* 36, 3341, 1993). In this method, 6-aminouracil is monoalkylated specifically at N3 of the uracil under Vorbruggen conditions. Following nitrosation, reduction, reaction with an aldehyde or carboxylic acid or carboxylic acid chloride, alkylation at N1 of the uracil, and ring closure, xanthines result.

In a particular case, anti-3-oxo-tricyclo[$2.2.1.0^{2,6}$] heptan-3-carboxylic acid can be easily synthesized from norbornadine, parafarmaldehyde, formic acid and sulfuric acid. (see, e.g., *J. Am. Chem. Soc.* 99, 4111, 1977; *Tetrahedron* 37 Supplement No.1 411, 1981. It can be easily resolved using Candida antartica Lipase A (*Tetrahedron Lett.* 37, 3975, 1996).

In many cases, the desired aldehydes, ketones, carboxylic acids and carboxylic acid chlorides are commercially available (e.g., from Aldrich Chemical Co., Inc., Milwaukee, Wisc.) or readily prepared from commercially available materials by well-known synthetic methods. Such synthetic methods include, but are not limited to, oxidation, reduction, hydrolysis, alkylation and Wittig homologation reactions.

The bicycloalkane carboxylic acids of the invention can also be prepared by published methods (see, e.g., *Aust. J. Chem.* 38, 1705, 1985; *Aust J. Chem.* 39, 2061, 1986; *J. Am. Chem. Soc.* 75, 637, 1953; *J. Am. Chem. Soc.* 86, 5183, 1964; *J. Am. Chem. Soc.* 102, 6862, 1980; *J. Org. Chem.* 46, 4795, 1981; and *J. Org. Chem.* 60, 6873, 1995).

Uses for the Adenosine Antagonist Compounds

Activation of adenosine receptors elicits many physiological responses, including reductions in renal blood flow, reductions in glomerular filtration rate, and increases in sodium reabsorption in kidney. Activation of adenosine receptors reduces heart rate, reduces conduction velocity, and reduces contractility. These, and the other effects of activation of adenosine receptors in other organs, are normal regulatory processes. However, these effects become pathological in many disease states. Thus, adenosine antagonists have extensive application in both prevention and treatment of disease. Diseases that can be prevented and/or treated with adenosine receptor antagonists include any conditions (a) marked by the presence of an abnormal level of adenosine and/or (b) requiring for treatment the inhibition or stimulation of adenosine production and/or release. Such conditions include, but are not limited to, congestive heart failure, cardio-pulmonary resuscitation, hemorrhagic shock, and other cardiac and circulatory disorders; degenerative disorders of the central nervous system; respiratory disorders (e.g., bronchial asthma, allergic lung diseases); and many diseases for which diuretic treatment is indicated (e.g., acute and chronic renal failure, renal insufficiency, hypertension). Degenerative illnesses such as Parkinson's disease, depression, traumatic brain damage, post-stroke neurological deficit, neonatal brain trauma, dyslexia, hyperactivity, and cystic fibrosis have all been linked to adenosine receptor activity. Other conditions in which treatment with adenosine receptor antagonists can have therapeutic utility include cirrhotic ascites, neonatal apnea, renal failure associated with traditional diuretic therapy, diabetes, and asthma.

Additionally, applicants have discovered that the administration of highly selective and potent adenosine A1 receptor antagonists, for example, can elicit a diuretic response when administered alone and can potentiate the diuretic response to traditional diuretics. In addition, administration of adenosine receptor antagonists with traditional diuretics attenuate the reduction of glomerular filtration rate induced by traditional diuretics. The claimed methods are applicable, for example, in edematous conditions, such as congestive heart failure and ascites.

Administration of the Adenosine Antagonist Compounds

The compounds can be administered to an animal (e.g., a mammal such as a human, non-human primate, horse, dog, cow, pig, sheep, goat, cat, mouse, rat, guinea pig, rabbit, hamster, gerbil, ferret, lizard, reptile, or bird). The compounds can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The compounds can be administered orally, intranasally, transdermally, intradermally, vaginally, intraaurally, intraocularly, buccally, rectally, transmucosally, or via inhalation, implantation (e.g., surgically), or intravenous administration.

Optionally, the compounds can be administered in conjunction with a non-adenosine modifying pharmaceutical composition (e.g., in combination with a non-adenosine modifying diuretic as described, for example, in co-pending application PCT/US99/08879 filed Apr. 23, 1999, incorporated herein by reference in its entirety).

The invention will be further described in the following examples, which do not limit the scope of the invention described in the claims.

EXAMPLES

Example 1

8-(5-Oxo-tricyclo[2.2.1.0$^{2,6}$]hept-3-yl)-1,3-dipropyl-3,7-dihydro-purine-2,6-dione Anti-3-oxotricyclo(2.2.1.0$^{2,6}$)heptane-7-carboxylic acid (837 mg) was taken in $CH_2Cl_2$ (20 ml) at 0° C. Triethyamine (1.74 ml), isobutylchloroformate (724 µl) were added and stirred at 0° C. for 15 min. 1,3-Dipropyl-5,6-diaminouracil HCl was added and stirred at 0° C. for 30 min and at room temperature overnight. The next day, the reaction mixture was diluted with water (50 ml) and extracted with $CH_2Cl_2$ (3×25 ml). The combined organic layer was washed with sat $NaHCO_3$, water, brine, and dried over $Na_2SO_4$. Concentration of the solvent gave a crude product, which was taken to next step without further purification. Mass (ES$^+$ 361).

5-Oxo-tricyclo[2.2.1.0$^{2,6}$]heptane-3-carboxylic acid (6-amino-2,4-dioxo-1,3-dipropyl-1,2,3,4-tetrahydro-pyrimidin-5-yl)-amide (360 mg) from step 1 was taken in 1:1 isopropanol:water (5 ml) and KOH (84 mg) was added. The reaction mixture was refluxed for one and half-hour. After cooling the reaction mixture to room temperature, iPrOH was removed by rotavap. The aqueous layer was neutralized with 2N HCl and extracted with ethyl acetate (3×50 ml). The combined organic layer was washed with water and brine and dried over $Na_2SO_4$. After concentration, the crude product was purified by silica gel chromatography, eluting with ethyl acetate:hexane (1:1). Yield (75 mg) Mass (ES$^+$ 343).

Example 2

Endo/exo 8-(5-Hydroxy-tricyclo[2.2.1.0$^{2,6}$]hept-3-yl)-1,3-dipropyl-3,7-dihydro-purine-2,6-dione 8-(5-Oxo-tricyclo[2.2.1.0$^{2,6}$]hept-3-yl)-1,3-dipropyl-3,7-dihydro-purine-2,6-dione (700 mg) was dissolved in MeOH (50 ml). $NaBH_4$ (100 mg) was added at 0° C. and stirred for 5 min. Water was added and stirred for 30 min. MeOH was removed by rotavap under reduced pressure. The reaction mixture was extracted with ethyl acetate, washed with water, brine, and dried over $MgSO_4$. Concentration gave 700 mg of a mixture of endo:exo alcohols in a 6:4 ratio.

Example 3

8-(5-Methylene-tricyclo[2.2.1.0$^{2,6}$]hept-3-yl)-1,3-dipropyl-3,7-dihydro-purine-2,6-dione Methyl-triphenyl-phosphonium bromide (2.08 g) was taken in THF (50 ml) at −78° C. nBuLi (3.66 ml, 1.6 M) was added slowly at −78° C. and stirred for 1 hr. 8-(5-Oxo-tricyclo[2.2.1.0$^{2,6}$]hept-3-yl)-1,3-dipropyl-3,7-dihydro-purine-2,6-dione (Example 1) (1 g) was dissolved in THF and added to the reaction mixture at −78° C. slowly. After the addition was over, the reaction mixture was allowed to warmed to room temperature slowly and stirred at room temperature overnight. The next day, the reaction mixture was quenched with 1N HCl and extracted with ethyl acetate (3×50 ml). The combined organic layer was washed with water, brine and dried over $Na_2SO_4$. After concentration the product was purified by silica gel column. Mass (ES$^+$ 341).

Example 4

8-(5-Methoxymethylene-tricyclo[2.2.1.0$^{2,6}$]hept-3-yl)-1,3-dipropyl-3,7-dihydro-purine-2,6-dione Methoxymethyl-triphenyl-phosphonium chloride (1.1 g) was taken in toluene (10 ml) at 0° C. Potassium bis(trimethylsilyl)amide (0.5 M in toluene, 12.8 ml) was added and stirred at 0° C. for 1 hr. 8-(5-Oxo-tricyclo[2.2.1.0$^{2,6}$]hept-3-yl)-1,3-dipropyl-3,7-dihydro-purine-2,6-dione (Example 1) (1 g) was added to the reaction mixture, which was then warmed to room temperature and stirred overnight. The next day, the reaction mixture was quenched with water, and extracted with ethyl acetate (3×50 ml). The combined organic layer was washed with water and brine, and dried over $Na_2SO_4$. After concentration, the crude product (620 mg) was purified by column. Mass (ES$^+$ 371).

Example 5

8-(5-endo Hydroxy-tricyclo[2.2.1.0$^{2,6}$]hept-3-yl)-1,3-dipropyl-3,7-dihydro-purine-2,6-dione Sodium borohydride (22 mg) was taken in MeOH (5 ml) at 0° C. 8-(5-Oxo-tricyclo[2.2.1.0$^{2,6}$]hept-3-yl)-1,3-dipropyl-3,7-dihydro-purine-2,6-dione (Example 1) (200 mg) in MeOH (5 ml) was added to reaction mixture at 0° C. After stirring at 0° C. for 1 hr, the reaction mixture was quenched with 1N HCl and extracted with ethyl acetate (3×25 ml). The combined organic layer was washed with water, brine and dried over $Na_2SO_4$. After concentration of the solvent, the product was purified by preparative HPLC. Mass (ES$^+$ 345) Product is a mixture of two isomers ratio (2:1). The major isomer is the endo hydroxyl compound.

Example 6

8-(5-exo Hydroxy-tricyclo[2.2.1.0$^{2,6}$]hept-3-yl)-1,3-dipropyl-3,7-dihydro-purine-2,6-dione To a solution of 8-(5-Oxo-tricyclo[2.2.1.0$^{2,6}$]hept-3-yl)-1,3-dipropyl-3,7-dihydro-purine-2,6-dione (Example 1) (2 g) in THF (40 ml) at −78° C. was added dropwise a solution of K-selectride (20 ml, 1M in THF). The mixture was stirred at −78° C. for 30 min, then allowed to warm to 0° C., quenched with water and extracted with ethyl acetate (3×50 ml). The combined organic layer was washed with brine and dried over MgSO$_4$. Filtered and concentrated under reduced pressure to give the desired product (1.97 g) as a 20:1 mixture of exo and endo alcohols. Mass (ES$^+$ 345).

Example 7

8-(5-endo-Hydroxymethyl-5-methyl-tricyclo [2.2.1.0$^{2,6}$]hept-3-yl)-1,3-dipropyl-3,7-dihydro-purine-2,6-dione and 8-(5-exo-Hydroxy-5-hydroxymethyl-tricyclo[2.2.1.0$^{2,6}$]hept-3-yl)-1,3-dipropyl-3,7-dihydro-purine-2,6-dione 8-(5-Methoxymethylene-tricyclo[2.2.1.0$^{2,6}$]hept-3-yl)-1, 3-dipropyl-3,7-dihydro-purine-2,6-dione (368 mg) was taken in THF (5 ml). 1N HCl (2 ml) was added to the reaction mixture and stirred at room temperature for 4 hrs. The reaction mixture was extracted with ethyl acetate (3×25 ml). The combined extract was washed with sat NaHCO$_3$, water, and brine, and dried over Na$_2$SO$_4$. The product was a mixture of endo and exo aldehydes, which was taken to next step without further purification.

The mixture of aldehydes was reduced using NaBH$_4$ in MeOH following the procedure of Example 5. The product mixture of endo and exo hydroxyl methyl compounds was separated by preparative HPLC. Mass (ES$^+$ 359).

The following compounds were prepared by the same methods:

Example 7a

Endo-8-(5-endo-Hydroxymethyl-5-methyl-tricyclo [2.2.1.0$^{2,6}$]hept-3-yl)-1,3-dipropyl-3,7-dihydro-purine-2,6-dione

Example 7b

Endo-8-(5-endo Hydroxymethyl-5-methyl-tricyclo [2.2.1.0$^{2,6}$]hept-3-yl)-1,3-dipropyl-3,7-dihydro-purine-2,6-dione

Example 8

8-(5-Hydroxy-5-hydroxymethyl-tricyclo[2.2.1.0$^{2,6}$] hept-3-yl)-1,3-dipropyl-3,7-dihydro-purine-2,6-dione 8-(5-Methylene-tricyclo[2.2.1.0$^{2,6}$]hept-3-yl)-1,3-dipropyl-3,7-dihydro-purine-2,6-dione (284 mg) was taken in acetone:water (1:1, 5 ml) at 0° C. OsO$_4$ (2 ml) was added and the mixture was stirred for 15 min. N-Methylmorpholine-N-oxide (120 mg) was added and the mixture was stirred at room temperature overnight. The next day the reaction mixture was quenched with NaHSO$_3$ solution, extracted with ethyl acetate (3×25 ml). Combined organic layer was washed with water, brine and dried over Na$_2$SO$_4$. After concentration the crude product was purified on a silica column. (ES$^+$ 375)

Example 9

Endo-5-(2,6-Dioxo-1,3-dipropyl-2,3,6,7-tetrahydro-1H-purin-8-yl)-tricyclo[2.2.1.0$^{2,6}$]heptane-3endo carboxylic acid 8-(5-endo Hydroxymethyl-5-methyl-tricyclo[2.1.1.0$^{2,6}$] hept-3-yl)-1,3-dipropyl-3,7-dihydro-purine-2,6-dione and 8-(5-exo Hydroxy-5-hydroxymethyl-tricyclo[2.2.1.0$^{2,6}$] hept-3-yl)-1,3-dipropyl-3,7-dihydro-purine-2,6-dione (100 mg) was taken in DMF (5 ml). PDC (232 mg) was added at 0° C. and stirred at 0° C. to room temperature overnight. The next day, another 232 mg of PDC was added stirred at room temperature for 24 hrs. DMF was removed under reduced pressure. Dissolved in sat NaHCO$_3$ solution and extracted with ethyl acetate (2×50 ml). Aqueous layer was acidified with 1N HCl and extracted with ethyl acetate (3×100 ml). Ethyl acetate layer was washed with brine, dried over Na$_2$SO$_4$, and concentrated. Mixture of exo and endo acids was separated by preparative HPLC. Mass (ES$^+$ 373).

The following compound was prepared by the same method:

Example 9a

Exo-5-(2,6-Dioxo-1,3-dipropyl-2,3,6,7-tetrahydro-1H-purin-8-yl)-tricyclo[2.2.1.0$^{2,6}$]heptane-3exo carboxylic acid

Example 10

[5-(2,6-Dioxo-1,3-dipropyl-2,3,6,7-tetrahydro-1H-purin-8-yl)-tricyclo[2.2.1.0$^{2,6}$]hept-3-ylidene]-acetic acid Methyl diethyl phosphono acetate (100 μl) was taken in toluene (5 ml) at 0° C. Potassium bis(trimethylsilyl)amide (0.5 M in toluene, 2.2 ml) was added and stirred at 0° C. for 1 hr. 8-(5-Oxo-tricyclo[2.2.1.0$^{2,6}$]hept-3-yl)-1,3-dipropyl-3, 7-dihydro-purine-2,6-dione (Example 1) (171 mg) dissolved in 5 ml of toluene was added to the reaction mixture and warmed to room temperature and stirred overnight. The next day, the reaction mixture was quenched with water, acidified with 1N HCl,extracted with ethyl acetate (2×100 ml). The combined organic layer was washed with water, brine and dried over Na$_2$SO$_4$. After concentration the crude product (156 mg) was taken to next step without further purification Mass (ES$^+$ 399).

The ester (156 mg) from step 1 was hydrolyzed using LiOH (34 mg). The product was purified by preparative HPLC. Yield (52 mg). Mass (ES$^+$ 385).

Example 11

[5-(2,6-Dioxo-1,3-dipropyl-2,3,6,7-tetrahydro-1H-purin-8-yl)-tricyclo[2.2.1.0$^{2,6}$]hept-3-yl]-acetic acid The product (100 mg) from step 1 of Example 10 was hydrogenated in EtOH (5 ml) using Pd/C 5% at 60 psi of H$_2$ for 24 hrs. Catalyst was filtered and the solvent was concentrated. The product was taken to the next step.

The ester (90 mg) from step 1 was hydrolyzed with LiOH (19 mg) in MeOH:H$_2$O (5:1, 5 ml) at room temperature overnight. The product was purified by preparative HPLC. Yield: 51 mg. Mass (ES$^+$ 387).

Example 12

8-(2-Oxo-bicyclo[2.2.1]hept-7-yl)-1,3-dipropyl-3,7-dihydro-purine-2,6-dione

2-Oxo-bicyclo[2.2.1]heptane-7-carboxylic acid (308 mg) was couple to 1,3-Dipropyl-5,6-diaminouracil.HCl (576 mg) and cyclized using the procedures from Example 1. Yield: 320 mg. Mass (ES$^+$ 345).

Example 13

8-(2-Hydroxy-bicyclo[2.2.1]hept-7-yl)-1,3-dipropyl-3,7-dihydro-purine-2,6-dione 8-(2-Oxo-bicyclo[2.2.1]hept-7-yl)-1,3-dipropyl-3,7-dihydro-purine-2,6-dione (200 mg) was reduced using NaBH$_4$ (44 mg) in MeOH (10 ml). Yield 120 mg. Mass (ES$^+$ 347).

Example 14

5-(2,6-Dioxo-1,3-dipropyl-2,3,6,7-tetrahydro-1H-purin-8-yl)-3-hydroxymethyl-tricyclo[2.2.1.0$^{2,6}$]heptane-3-carboxylic acid

Anti-3-oxotricyclo(2.2.1.0$^{2,6}$)heptane-7-carboxylic acid (2.0 g) was taken in MeOH (50 ml) and conc. H$_2$SO$_4$ (0.2 ml) was added and refluxed overnight. The next day, after cooling the reaction mixture was poured into sat NaHCO$_3$ solution and extracted with ethyl acetate. Concentration of ethyl acetate gave 2.61 g of 5,5-Dimethoxy-tricyclo[2.2.1.0$^{2,6}$]heptane-3-carboxylic acid methyl ester.

5,5-Dimethoxy-tricyclo[2.2.1.0$^{2,6}$]heptane-3-carboxylic acid methyl ester (1.01 g) from step 1 was taken in dry THF (20 ml) at −78° C. and LDA (3.53 ml, 2M in THF) was added dropwise. The mixture was at −78° C. for 1 hr. Next BOMCl (2.29 g) was added dropwise. After 30 min at −78° C. the mixture was warmed to 0° C. and stirred for 1 hr. The reaction was quenched with sat NH$_4$Cl and extracted with ethyl acetate (2×50 ml). After concentration the crude product was take-up in THF (20 ml) and 1N HCl (5 ml) was added. The reaction mixture was stirred at room temperature for 1 hr, dilute with water extracted with ethyl acetate. Ethyl acetate was washed with brine and dried over MgSO$_4$. After concentration the product was purified on a silica column. Yield 515 mg.

Step 3: 3-Benzyloxymethyl-5-oxo-tricyclo[2.2.1.0$^{2,6}$]heptane-3-carboxylic acid methyl ester from step 2 was converted to 3-Benzyloxymethyl-5-formyl-tricyclo[2.2.1.0$^{2,6}$]heptane-3-carboxylic acid methyl ester following the procedures from Example 4 and Example 7.

Into a solution of 3-benzyloxymethyl-5-formyl-tricyclo[2.2.1.0$^{2,6}$]heptane-3-carboxylic acid methyl ester (475 mg) in 10 ml of t-BuOH and 8 ml of 2-methyl-but-2-ene at 0° C. was added NaClO$_2$ (904 mg) and NaH$_2$PO$_4$H$_2$O (1.37 g) in water (5 ml). The mixture was stirred at room temperature for 5 hrs. The reaction was acidified with HOAc and extracted with ethyl acetate, washed with water and dried. Concentration gave the desired acid (175 mg).

3-Benzyloxymethyl-tricyclo[2.2.1.0$^{2,6}$]heptane-3,5-dicarboxylic acid 3-methyl ester (168 mg) from above was coupled to 1,3 dipropyl-5,6-diaminouracil.HCl (263 mg) using EDC (191 mg), DIEA (258 mg)in CH$_2$Cl$_2$ (20 ml) at room temperature overnight. After workup the product was cyclized using aq. KOH in iPrOH.

3-Benzyloxymethyl-5-(2,6-dioxo-1,3-dipropyl-2,3,6,7-tetrahydro-1H-purin-8-yl)-tricyclo[2.2.1.0$^{2,6}$]heptane-3-carboxylic acid (50 mg) was hydrogenated in ethyl acetate using Pd/C 5% under 1 atm of H$_2$ overnight. The catalyst was filtered through silica eluting with 10% MeOH:CHCl$_3$. Yield 31 mg. Mass (ES$^+$ 403).

Example 15

[7-(2,6-Dioxo-1,3-dipropyl-2,3,6,7-tetrahydro-1H-purin-8-yl)-bicyclo[2.2.1]hept-2-ylidene]-acetic acid

8-(2-Oxo-bicyclo[2.2.1]hept-7-yl)-1,3-dipropyl-3,7-dihydro-purine-2,6-dione was converted to the title compound using the procedure from Example 10. Mass (ES$^+$ 387).

Example 16

Endo 2-tert-Butoxycarbonylamino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester

To a solution of DIC (126 mg), and DMAP (122 mg) in CH$_2$Cl$_2$ (10 ml) at 0° C. was added Boc-L-Valine (217 mg). The mixture was stirred for 30 min and then 8-(5-endo hydroxy-tricyclo[2.2.1.0$^{2,6}$]hept-3-yl)-1,3-dipropyl-3,7-dihydro-purine-2,6-dione (110 mg) was added. The resulting mixture was stirred at room temperature overnight. The next day, the reaction was diluted with ethyl acetate, washed with in HCl, sat NaHCO$_3$, and brine, and dried over MgSO$_4$. The product was filtered, concentrated, and purified on silica to give the desired compound. Yield 155 mg Mass (ES$^+$ 544).

Example 16a

Exo-2-tert-Butoxycarbonylamino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester.

Example 17

Endo-2-Amino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester HCl

Endo 2-tert-Butoxycarbonylamino-3-methyl-butyric acid 5-(2,6-dioxo-1,3-dipropyl-2,3,6,7-tetrahydro-1H-purin-8-yl)-tricyclo[2.2.1.0$^{2,6}$]hept-3yl ester (120 mg) was taken in THF (2 ml). 1M HCl in ether (2 ml) was added and the reaction mixture was stirred at room temperature overnight. The solvent was removed under reduced pressure. The crude residue was taken up in THF, the product was precipitated by adding ether. Yield 55 mg. Mass (ES$^+$ 444).

Example 18

(+) Endo 8-(5-Hydroxy-tricyclo[2.2.1.0$^{2,6}$]hept-3-yl)-1,3-dipropyl-3,7-dihydro-purine-2,6-dione

(+) Anti-3-oxotricyclo(2.2.1.0$^{2,6}$)heptane-7-carboxylic acid, prepared using the procedure described in *Tetrahedron Letters*, 37:3975–3976, 1996, was coupled to 1,3-dipropyl-5,6-diaminouracil and cyclized following the procedure described in Example 1. The resulting ketone was reduced to an alcohol using the procedure from Example 5.

Example 18a

(−) Endo Endo 8-(5-Hydroxy-tricyclo[2.2.1.0$^{2,6}$]hept-3-yl)-1,3-dipropyl-3,7-dihydro-purine-2,6-dione

Example 19

Exo 2-Amino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester; compound with trifluoro-acetic acid

Exo-2-tert-Butoxycarbonylamino-3-methyl-butyric acid 5-(2,6-dioxo-1,3-dipropyl-2,3,6,7-tetrahydro-1H-purin-8-yl)-tricyclo[2.2.1.02,6]hept-3-yl ester (100 mg) was treated with CH$_2$Cl$_2$:TFA(1:1, 5 ml) at room temperature overnight. The solvent was removed under reduced pressure and the crude residue was purified by HPLC. Mass (ES$^+$ 444).

Example 20

Endo-[5-(2,6-Dioxo-1,3-dipropyl-2,3,6,7-tetrahydro-1H-purin-8-yl)-tricyclo[2.2.1.0$^{2,6}$]hept-3-yloxy]-acetic acid

8-(5-Oxo-tricyclo[2.2.1.0$^{2,6}$]hept-3-yl)-1,3-dipropyl-3,7-dihydro-purine-2,6-dione (1 g) was taken in DMF (10 ml)

Cs$_2$CO$_3$ (5.85 g) was added followed by BOMCl (810 μl) at room temperature. The reaction mixture was stirred at room temperature overnight. Cs$_2$CO$_3$ was filtered off, and the DMF was removed under reduced pressure. The crude product was purified on silica column.

The resulting ketone was reduced using NaBH$_4$ following the example. Yield (1.3 g) mixture of endo and exo alcohols.

NaH (240 mg, 60% suspension in mineral oil) was washed with dry pentane 3 times and taken in dry THF at 0° C. Mixture of alcohols from above (500 mg) in THF (5 ml) was added to the reaction and stirred at 0° C. for 1 hr. Bromo-t-butylacetate (420 mg) was added at 0° C. and stirred at 0° C. to room temperature overnight. The next day, the reaction mixture was heated at 60° C. for 3 hr. After cooling to room temperature, the reaction mixture was diluted with water, extracted with ethyl acetate (3×50 ml). The combined ethyl acetate layer was washed with water, brine and dried over Na$_2$SO$_4$. After concentration the crude mixture was taken to next step.

Product from above was taken in ethyl acetate (5 ml) and 100 mg of Pd/C 10%, 1 ml of conc. HCl was added. The reaction mixture was hydrogenated under 60 psi H$_2$ overnight. The catalyst was filtered off and the solvent was removed by rotavap. The residue was taken in 5 ml of MeOH and LiOH (100 mg) was added. The reaction mixture was stirred at room temperature overnight. The next day, the solvent was removed, diluted with water, extracted with ethyl acetate (2×50 ml). The aqueous layer was acidified with 1N HCl, extracted with ethyl acetate (3×50 ml). Ethyl acetate layer was washed with water and brine, and dried over Na$_2$SO$_4$. Concentration of the ethyl acetate layer gave 390 mg mixture of endo and exo products that was separated by HPLC. Mass (ES$^+$ 403).

Example 20a

Exo-[5-(2,6-Dioxo-1,3-dipropyl-2,3,6,7-tetrahydro-1H-purin-8-yl)tricyclo[2.2.1.02,6]hept-3-yloxy]-acetic acid Example 21

(−) Endo-2-tert-Butoxycarbonylamino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester (−)-Endo 8-(5-Hydroxy-tricyclo[2.2.1.0$^{2,6}$]hept-3-yl)-1,3-dipropyl-3,7-dihydro-purine-2,6-dione was coupled to Boc-L-Valine using the procedure from Example 16.

Example 22

(−) Endo 2-Amino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester HCl (−) Endo-2-tert-Butoxycarbonylamino-3-methyl-butyric acid 5-(2,6-dioxo-1,3-dipropyl-2,3,6,7-tetrahydro-1H-purin-8-yl)-tricyclo[2.2.1.0$^{2,6}$]hept-3-yl ester was converted to the product following the procedure from example Example 17. Mass (ES$^+$ 444).

Example 23

8-[5-(3-Dimethylamino-propylidene)-tricyclo[2.2.1.0$^{2,6}$]hept-3-yl]-1,3-dipropyl-3,7-dihydro-purine-2,6-dione; compound with trifluoro-acetic acid (3-Dimethylamino-propyl)-triphenyl-phosphonium; bromide (514 mg) was taken in THF (20 ml) at 0° C. Potassium bis(trimethylsilyl)amide (0.5 M in toluene, 5 ml) was added and stirred at 0° C. for 1 hr. 8-(5-Oxo-tricyclo[2.2.1.0$^{2,6}$]hept-3-yl)-1,3-dipropyl-3,7-dihydro-purine-2,6-dione (342 mg) dissolved in 5 ml of THF was added to the reaction mixture at 0° C. The reaction mixture was stirred at 0° C. to room temperature overnight. The next day, the THF was removed by rotavap under reduced pressure, the residue was dissolved in water (10 ml), acidified with 1N HCl, and extracted with ethyl acetate (2×100 ml). The aqueous layer was concentrated and purified by HPLC. Yield 140 mg. Mass (ES$^+$ 412).

Example 24

8-[5-(3-Dimethylamino-propyl)-tricyclo[2.2.1.0$^{2,6}$]hept-3-yl]-1,3-dipropyl-3,7-dihydro-purine-2,6-dione 8-[5-(3-Dimethylamino-propylidene)-tricyclo[2.2.1.0$^{2,6}$]hept-3-yl]-1,3-dipropyl-3,7-dihydro-purine-2,6-dione; compound with trifluoro-acetic acid was hydrogenated under 60 psi using Pt/C 5% in EtOH (10 ml) and 1 ml conc. HCl overnight. Catalyst was filtered and solvent was removed under reduced pressure. Crude product was purified by HPLC Yield 30 mg. Mass (ES$^+$ 414).

Example 25

8-(4-Hydroxy-bicyclo[3.2.1]oct-6-yl)-1,3-dipropyl-3,7-dihydro-purine-2,6-dione

4-Acetoxy-bicyclo[3.2.1]octane-6-carboxylic acid (425 mg) was taken in CH$_2$Cl$_2$ (5 ml) at 0° C. TEA (700 μl) and i-butylchloroformate (285 μl) were added and stirred at 0° C. for 30 min. 1,3-Dipropyl-5,6-diaminouracil.HCl (524 mg) was added and stirred at 0° C. for 30 min and at room temperature overnight. The next day, the reaction was diluted with CH$_2$Cl$_2$ (25 ml), washed with water, dried over Na$_2$SO$_4$, and concentrated. The crude product (820 mg) was taken to next step without further purification.

The product was cyclized in i-PrOH/water (1:1, 15 ml) using KOH (280 mg) under reflux for 1 hr. Followed the procedure from Example 1. Yield 450 mg. Mass (ES$^+$ 361).

Example 26

8-(4-Oxo-bicyclo[3.2.1]oct-6-yl)-1,3-dipropyl-3,7-dihydro-purine-2,6-dione 8-(4-Hydroxy-bicyclo[3.2.1]oct-6-yl)-1,3-dipropyl-3,7-dihydro-purine-2,6-dione (140 mg) from step 1 was taken in CH$_2$Cl$_2$ (5 ml). Celite (2 g) was added, followed by PCC (90 mg) and stirred at room temperature for 1 hr. Additional PCC (90 mg) was added and stirred for 2 hrs at room temperature. The reaction mixture was diluted with ether (100 ml) and filtered through celite and concentrated. Purified on silica column eluted with ethyl acetate:hexane (25:75) to yield 65 mg of the desired product. Mass (ES$^+$ 369).

Example 27

8-(4-Hydroxy-4-methyl-bicyclo[3.2.1]oct-6-yl)-1,3-dipropyl-3,7-dihydro-purine-2,6-dione 8-(4-Oxo-bicyclo[3.2.1]oct-6-yl)-1,3-dipropyl-3,7-dihydro-purine-2,6-dione (51 mg) was taken in THF (3 ml) at 0° C. CH$_3$MgBr (1 ml, 3.0 M) was added and stirred for 2 hrs. The reaction was quenched with sat. NH$_4$Cl, and extracted with ethyl acetate. The organic layer was washed with water, brine, and dried over $Na_2SO_4$. Concentration followed by purification on silica column gave the desired product. Mass ($ES^+$ 375).

Example 28

8-(3-Oxo-2-aza-bicyclo[3.2.1]oct-7-yl)-1,3-dipropyl-3,7-dihydro-purine-2,6-dione 8-Bicyclo[2.2.1]hept-5-en-2-yl-1,3-dipropyl-3,7-dihydro-purine-2,6-dione (5 g) was treated with NaH (878 mg) in THF at 0° C. After one hour, BOMCl (2.52 ml) was added dropwise and stirred overnight. The next day, the reaction was quenched with water, extracted with ethyl acetate, washed with water and dried over $Na_2SO_4$. After concentration, the crude product was taken to next step.

7-Benzyloxymethyl-8-bicyclo[2.2.1]hept-5-en-2-yl-1,3-dipropyl-3,7-dihydro-purine-2,6-dione (5 g) from step 1 was taken in THF (25 ml) at 0° C. $BH_3THF$ (12 ml, 1 M) was added. After two hours, 6N NaOH (1 ml) and $H_2O_2$ (12 ml) were added and stirred for another 2 hrs. The reaction mixture was acidified with 1N HCl and extracted with ethyl acetate. The organic layer was washed with water, brine and dried over $Na_2SO_4$. Concentration of the organic layer gave a mixture of two products, which were separated by column chromatography. The less polar compound, 7-benzyloxymethyl-8-(6-hydroxy-bicyclo[2.2.1]hept-2-yl)-1,3-dipropyl-3,7-dihydro-purine-2,6-dione, (major product) yield 1.7 g. Mass ($ES^+$ 467).

7-Benzyloxymethyl-8-(6-hydroxy-bicyclo[2.2.1]hept-2-yl)-1,3-dipropyl-3,7-dihydro-purine-2,6-dione (1.6 g) was oxidized using PCC (855 mg) following the procedure from Example 26.

7-Benzyloxymethyl-8-(6-oxo-bicyclo[2.2.1]hept-2-yl)-1,3-dipropyl-3,7-dihydro-purine-2,6-dione (435 mg) from step 3 was taken in acetic acid (5 ml). Hydroxylamino-O-sulfonic acid (211 mg) was added and refluxed for 3 hrs. After cooling, the reaction mixture was extracted with ethyl acetate (3×25 ml). The organic layer was washed with sat. $NaHCO_3$, water, brine and dried over $Na_2SO_4$. Solvent was removed by rotavap and the desired product was purified on a silica column. Mass ($ES^+$ 360).

Example 29

8-(2-Oxo-3-aza-bicyclo[3.2.1]oct-8-yl)-1,3-dipropyl-3,9-dihydro-purine-2,6-dione Into a solution of $NaN_3$ (65 mg) in $CHCl_3$ (2 ml) was added $H_2SO_4$ (0.5 ml). The resulting solution was cooled to 0° C. 8-(2-Oxo-bicyclo[2.2.1]hept-7-yl)-1,3-dipropyl-3,7-dihydro-purine-2,6-dione (173 mg) in $CHCl_3$ (3 ml) was added. The resulting solution was stirred at room temperature for 3 hrs. The reaction mixture was poured over ice and neutralized with $NaHCO_3$, extracted with ethyl acetate (3×25 ml). The combined extract was dried over $MgSO_4$, filtered, and concentrated. The crude product was purified by recrystallization from MeOH. Yield 155 mg. Mass ($ES^+$ 360).

Example 30

[8-(2,6-Dioxo-1,3-dipropyl-2,3,6,7-tetrahydro-1H-purin-8-yl)-3-aza-bicyclo[3.2.1]oct-3-yl]-acetic acid benzyl ester 8-(2-Oxo-3-aza-bicyclo[3.2.1]oct-8-yl)-1,3-dipropyl-3,9-dihydro-purine-2,6-dione (85 mg) was taken in THF (2 ml) and 1 ml of 1M LAH in ether was added and refluxed overnight. The next day, after cooling the reaction was quenched with ice, 1N KOH was added, extracted with ethyl acetate (3×25 ml). Combined extract was washed with brine and dried over $MgSO_4$. The solvent was removed under reduced pressure. The product (14 mg) was taken in 2 ml of $CH_2Cl_2$, Bromoacetic acid benzyl ester (23 mg) was added and stirred at room temperature overnight. The next day, the reaction mixture was basified with 1N NaOH, extracted with ethyl acetate. The crude product was purified on a silica column. Yield (7 mg) Mass ($ES^+$ 494).

Example 31

8-(3-Oxo-2-aza-bicyclo[3.2.1]oct-8-yl)-1,3-dipropyl-3,7-dihydro-purine-2,6-dione 8-(2-Oxo-bicyclo[2.2.1]hept-7-yl)-1,3-dipropyl-3,7-dihydro-purine-2,6-dione (278 mg) was converted to the product (185 mg) following the procedure from Example 27. Mass ($ES^+$ 360).

Example 32

8-(3-Oxo-4-aza-tricyclo[3.2.1.0$^{2,7}$]oct-6-yl)-1,3-dipropyl-3,7-dihydro-purine-2,6-dione 8-(5-Oxo-tricyclo[2.2.1.0$^{2,6}$]hept-3-yl)-1,3-dipropyl-3,7-dihydro-purine-2,6-dione (150 mg) was converted to the product (135 mg) following the procedure from Example 27. Mass ($ES^+$ 358).

Example 33

8-(3-Oxo-bicyclo[3.2.1]oct-8-yl)-1,3-dipropyl-3,7-dihydro-purine-2,6-dione

3-Oxo-bicyclo[3.2.1]octane-8-carboxylic acid ethyl ester, prepared using the lit procedure (*J. Org. Chem.* 1997, 62, 174–181), was hydrolyzed to the keto acid using KOH in MeOH.

3-Oxo-bicyclo[3.2.1]octane-8-carboxylic acid (205 mg) from step 1 was coupled to diaminouracil HCl (395 mg) using EDC (287 mg) in $CH_2Cl_2$ in the presence of DIEA (490 mg) and cyclized in iPrOH (50 ml), 1N KOH (10 ml) at reflux overnight. The crude product was purified on silica column. Yield (210 mg). Mass ($ES^+$ 359).

Example 34

Exo 8-(3-Hydroxy-bicyclo[3.2.1]oct-8-yl)-1,3-dipropyl-3,7-dihydro-purine-2,6-dione 8-(3-Oxo-bicyclo[3.2.1]oct-8-yl)-1,3-dipropyl-3,7-dihydro-purine-2,6-dione (30 mg) was dissolved in MeOH (2 ml) and $NaBH_4$ (20 mg) was added to the reaction at 0° C. and stirred for 10 min. The reaction was quenched with water and extracted with ethyl acetate. The organic layer was dried over $MgSO_4$ and concentrated. The crude products (mixture of endo and exo alcohols) were purified by HPLC. Exo alcohol 4 mg. Mass ($ES^+$ 361)

Example 34a

Endo 8-(3-Hydroxy-bicyclo[3.2.1]oct-8-yl)-1,3-dipropyl-3,7-dihydro-purine-2,6-dione. Endo alcohol (12 mg). Mass ($ES^+$ 361)

Example 35

3-(2,6-Dioxo-1,3-dipropyl-2,3,6,7-tetrahydro-1H-purin-8-yl)-bicyclo[3.2.1]oct-2-ene-8-carboxylic acid Into a solution of 3-Oxo-bicyclo[3.2.1]octane-8-carboxylic acid ethyl ester (100 mg), prepared using the procedure of *J. Org. Chem.* 62:174–181, 1997, in THF (5 ml) at −78° C., was added dropwise a solution of LDA (0.3 ml, 2M). The reaction mixture was stirred at −78° C. for 30 min. The resulting enolate was quenched with Bis (trifluoromethylsulfonyl)-amino benzene (214 mg). After another 30 min at −78° C., the reaction mixture was quenched with sat. NH$_4$Cl. The reaction mixture was taken in ethyl acetate, washed with water, brine, and dried over MgSO$_4$. The solvent was removed under reduced pressure, the crude product was taken to next step without further purification.

The product from step 1 was taken in DMF (10 ml). 1,3-Dipropyl-5,6-diaminouracil.HCl (263 mg), PPh$_3$ (15 mg), Pd(OAc)$_2$ (7 mg), DIEA (194 mg) were added. The reaction mixture was stirred at 100° C. under a slow bubbling of carbon monoxide for 1 day. The solution was cooled to room temperature, diluted with ethyl acetate, washed with 1N HCl, brine, and dried over MgSO$_4$. The solvent was removed under reduced pressure, the crude product was taken to next step without further purification.

The product from step 2 was cyclized in iPrOH (15 ml), 1N KOH (5 ml) under reflux overnight. After cooling to room temperature, the solvent was concentrated under reduced pressure, acidified with 1N HCl, saturated with solid NaCl, extracted with ethyl acetate, washed with brine and dried over MgSO$_4$. After concentration, the crude product was purified on silica column. Yield (50 mg). Mass (ES$^+$ 387).

ExampleExample 35a

Example3-(2,6-Dioxo-1,3-dipropyl-2,3,6,7-tetrahydro-1H-purin-8-yl)-8-aza-bicyclo[3.2.1]oct-2-ene-8-carboxylic acid ethyl ester. Mass (ES$^+$ 416).

ExampleExample 36

Example3-(2,6-Dioxo-1,3-dipropyl-2,3,6,7-tetrahydro-1H-purin-8-yl)-bicyclo[3.2.1]octane-8-carboxylic acid 3-(2,6-Dioxo-1,3-dipropyl-2,3,6,7-tetrahydro-1H-purin-8-yl)-bicyclo[3.2.1]oct-2-ene-8-carboxylic acid (Example 29) was hydrogenated using Pd/C in ethyl acetate. Mass (ES$^+$ 389).

ExampleExample 37

Example8-(8-Oxo-bicyclo[3.2.1]oct-3-yl)-1,3-dipropyl-3,7-dihydro-purine-2,6-dione The product (390 mg) from Example 35, was taken in THF (10 ml) 6N HCl (3 ml) and heated to reflux overnight. The next day, after cooling to room temperature, poured over ice, neutralized with NaHCO$_3$, extracted with ethyl acetate, washed with brine and dried over MgSO$_4$. Filtered, concentrated, and purified on silica. Yield (321 mg). Mass (ES$^+$ 359).

ExampleExample 38

Example8-(8-Hydroxy-bicyclo[3.2.1]oct-3-yl)-1,3-dipropyl-3,7-dihydro-purine-2,6-dione 8-(8-Oxo-bicyclo[3.2.1]oct-3-yl)-1,3-dipropyl-3,7-dihydro-purine-2,6-dione (25 mg) was reduced using NaBH$_4$ (30 mg) in MeOH at 0° C. The product was purified by HPLC. Yield (7 mg). Mass (ES$^+$ 361).

ExampleExample 39

Example2-[3-(2,6-Dioxo-1,3-dipropyl-2,3,6,7-tetrahydro-1H-purin-8-yl)-bicyclo[3.2.1]oct-8-yl]-malonic acid 8-(8-Hydroxy-bicyclo[3.2.1]oct-3-yl)-1,3-dipropyl-3,7-dihydro-purine-2,6-dione (30 mg) taken in CHCl$_3$ (5 ml). To this solution Meldrum's acid (58 mg), piperidine (10 mg) were added and heated to reflux overnight. The next day, after cooling to room temperature, diluted with ethyl acetate, washed with 1N HCl, sat NaHCO$_3$, brine, and dried. The solvent was removed under reduced pressure, the crude residue was taken up in MeOH, cooled to 0° C., NaBH$_4$ (30 mg) was added, the mixture was stirred for 15 min. The reaction was diluted with 1N HCl, extracted with ethyl acetate. The organic layer was washed with brine, dried over MgSO$_4$, and concentrated. The residue was taken up in THF (5 ml) and 4N HCl (5 ml) was added and stirred for 1 day. The reaction mixture was extracted with ethyl acetate, washed with brine, and concentrated. The crude product was purified by HPLC. Yield (6 mg). Mass (ES$^+$ 447).

ExampleExample 40

Example8-[3-(2-Dimethylamino-ethylamino)-bicyclo[3.2.1]oct-8-yl]-1,3-dipropyl-3,7-dihydro-purine-2,6-dione; compound with trifluoro-acetic acid To a solution of 8-(3-Oxo-bicyclo[3.2.1]oct-8-yl)-1,3-dipropyl-3,7-dihydro-purine-2,6-dione (60 mg) in CH$_2$Cl$_2$ (10 ml) at 0° C. were added N1,N1-Dimethyl-ethane-1,2-diamine (100 mg), Na(OAc)$_3$BH (100 mg), and HOAc (5 drops). The reaction mixture was stirred room temperature overnight. The next day, the reaction was quenched with water, acidified with 1N HCl. The aqueous layer was washed with CH$_2$Cl$_2$, then neutralized with 1N KOH, extracted with ethyl acetate (3×25 ml), washed with brine, dried over MgSO$_4$, and concentrated. The crude residue was purified by Preparative HPLC. Yield (31 mg) Mass (ES$^+$ 431).

ExampleExample 40a

Example[3-(2,6-Dioxo-1,3-dipropyl-2,3,6,7-tetrahydro-1H-purin-8-yl)-bicyclo[3.2.1]oct-8-ylamino]-acetic acid ethyl ester. Mass (ES$^+$ 446)

ExampleExample 40b

Example8-[8-(2-Dimethylamino-ethylamino)-bicyclo[3.2.1]oct-3-yl]-1,3-dipropyl-3,7-dihydro-purine-2,6-dione; compound with trifluoroacetic acid 8-(8-Oxo-bicyclo[3.2.1]oct-3-yl)-1,3-dipropyl-3,7-dihydro-purine-2,6-dione. Mass (ES$^+$ 431)

ExampleExample 40c

Example1-[3-(2,6-Dioxo-1,3-dipropyl-2,3,6,7-tetrahydro-1H-purin-8-yl)-bicyclo[3.2.1]oct-8-yl]-pyrrolidine-2-carboxylic acid methyl ester; compound with trifluoro-acetic acid. Mass (ES$^+$ 472)

Example 40d 8-(8-Morpholin-4-yl-bicyclo[3.2.1]oct-3-yl)-1,3-dipropyl-3,7-dihydro-purine-2,6-dione; compound with trifluoro-acetic acid. Mass (ES$^+$ 430)

Example 40e 8-(8-Allylamino-bicyclo[3.2.1]oct-3-yl)-1,3-dipropyl-3,7-dihydro-purine-2,6-dione; compound with trifluoro-acetic acid. Mass (ES$^+$ 400)

Example 40f

8-[8-(2-Piperidin-1-yl-ethylamino)-bicyclo[3.2.1]oct-3-yl]-1,3-dipropyl-3,7-dihydro-purine-2,6-dione; compound with trifluoro-acetic acid. Mass (ES$^+$ 471)

Example 40g

8-[8-(2-Morpholin-4-yl-ethylamino)-bicyclo[3.2.1]oct-3-yl]-1,3-dipropyl-3,7-dihydro-purine-2,6-dione; compound with trifluoro-acetic acid. Mass (ES$^+$ 473)

Example 40h

N-{2-[3-(2,6-Dioxo-1,3-dipropyl-2,3,6,7-tetrahydro-1H-purin-8-yl)-bicyclo[3.2.1]oct-8-ylamino]-ethyl}-acetamide; compound with trifluoro-acetic acid. Mass (ES$^+$ 445)

Example 40i

8-[8-(3-Dimethylamino-propylamino)-bicyclo[3.2.1]oct-3-yl]-1,3-dipropyl-3,7-dihydro-purine-2,6-dione; compound with trifluoro-acetic acid. Mass (ES$^+$ 445)

Example 40j

8-[8-(3-Morpholin-4-yl-propylamino)-bicyclo[3.2.1]oct-3-yl]-1,3-dipropyl-3,7-dihydro-purine-2,6-dione; compound with trifluoro-acetic acid. Mass (ES$^+$ 487)

Example 40k

8-[8-(3-Imidazol-1-yl-propylamino)-bicyclo[3.2.1]oct-3-yl]-1,3-dipropyl-3,7-dihydro-purine-2,6-dione; compound with trifluoro-acetic acid. Mass (ES$^+$ 468)

Example 40l

8-{8-[3-(2-Oxo-pyrrolidin-1-yl)-propylamino]-bicyclo[3.2.1]oct-3-yl}-1,3-dipropyl-3,7-dihydro-purine-2,6-dione; compound with trifluoro-acetic acid. Mass (ES$^+$ 468)

Example 41

8-(8-(1,4-dioxa-spiro 4-bicyclo[3.2.1]oct-3-yl)-1,3-dipropyl-3,7-dihydro-purine-2,6-dione Into a solution of 1-cyclopent-1-enyl-pyrrolidine (1.01 g), triethylamine (0.82 g), in CH$_3$CN (20 ml) was added a solution of 3-bromo-2-bromomethyl-propionic acid ethyl ester (2.03 g) in CH$_3$CN (10 ml). The reaction mixture was then heated to reflux overnight, cooled to room temperature, 5%HOAc (5 ml) was added then heated to reflux for 30 min. Cooled to room temperature diluted with ethyl acetate, washed with 1N HCl, sat NaHCO$_3$, brine, then dried. The solvent was removed under reduced pressure, the crude was taken up in ethylene glycol (30 ml), TsOH (50 mg) was added, the mixture was heated to reflux 1 day. Cooled to room temperature, diluted with ethyl acetate, washed with water, brine, and dried. After concentration the crude product was purified on silica to give 1.90 g.

The product from step 1 was taken in THF (30 ml), MeOH (30 ml), 1N KOH (30 ml) and heated at 50° C. overnight. The next day, cooled to room temperature, concentrated, acidified with 1N HCl, saturated with solid NaCl, extracted with ethyl acetate, washed with brine, concentrated.

The product from step 2 (Ketal acid) was coupled to diamino uracil HCl using EDC, DIEA in methylene chloride and cyclized using KOH in I-PrOH water. Mass(ES$^+$403)

Example 42

[3-(2,6-Dioxo-1,3-dipropyl-2,3,6,7-tetrahydro-1H-purin-8-yl)-bicyclo[3.2.1]oct-8-ylamino]-acetic acid

[3-(2,6-Dioxo-1,3-dipropyl-2,3,6,7-tetrahydro-1H-purin-8-yl)-bicyclo[3.2.1]oct-8-ylamino]-acetic acid ethyl ester (Example 40a) was hydrolyzed using 1N KOH in MeOH/THF. Mass (ES$^+$418)

Example 43

Exo-3-(2,6-Dioxo-1,3-dipropyl-2,3,6,7-tetrahydro-1H-purin-8-yl)-8-aza-bicyclo[3.2.1]octane-8-carboxylic acid ethyl ester 3-(2,6-Dioxo-1,3-dipropyl-2,3,6,7-tetrahydro-1H-purin-8-yl)-8-aza-bicyclo[3.2.1]oct-2-ene-8-carboxylic acid ethyl ester was hydrogenated using 10% Pd/C in MeOH. 1:3 mixture of endo and exo products was formed. The products were separated by HPLC. Exo isomer. Mass (ES$^+$418).

Example 43a

Endo-3-(2,6-Dioxo-1,3-dipropyl-2,3,6,7-tetrahydro-1H-purin-8-yl)-8-aza-bicyclo[3.2.1]octane-8-carboxylic acid ethyl ester

Example 44

Endo-8-(8-Aza-bicyclo[3.2.1]oct-3-yl)-1,3-dipropyl-3,7-dihydro-purine-2,6-dione; compound with trifluoro-acetic acid A mixture of Exo-3-(2,6-Dioxo-1,3-dipropyl-2,3,6,7-tetrahydro-1H-purin-8-yl)-8-aza-bicyclo[3.2.1]octane-8-carboxylic acid ethyl ester and Endo-3-(2,6-Dioxo-1,3-dipropyl-2,3,6,7-tetrahydro-1H-purin-8-yl)-8-aza-bicyclo[3.2.1]octane-8-carboxylic acid ethyl ester (1:3) was taken in 10 ml of $CH_2Cl_2$. TMSI (1 ml) was added and stirred at room temperature for 48 hrs. MeOH (3 ml) was added and taken up in ethyl acetate, washed with sat $NaHCO_3$, washed with 10% solution of $Na_2S_2O_3$, brine, and dried over $MgSO_4$. Filtered and concentrated. Purified by HPLC Endo isomer. Mass ($ES^+346$).

Example 44a

Exo-8-(8-Aza-bicyclo[3.2.1]oct-3-yl)-1,3-dipropyl-3,7-dihydro-purine-2,6-dione; compound with trifluoro-acetic acid. Exo isomer Mass ($ES^+$ 346)

Example 45

1-[3-(2,6-Dioxo-1,3-dipropyl-2,3,6,7-tetrahydro-1H-purin-8-yl)-bicyclo[3.2.1]oct-8-yl]pyrrolidine-2-carboxylic acid; compound with trifluoro-acetic acid 1-[3-(2,6-Dioxo-1,3-dipropyl-2,3,6,7-tetrahydro-1H-purin-8-yl)-bicyclo[3.2.1]oct-8-yl]-pyrrolidine-2-carboxylic acid methyl ester (Example 40c) was hydrolyzed with 1 N KOH in THF. Mass ($ES^+458$)

Example 46

8-(8-Amino-bicyclo[3.2.1]oct-3-yl)-1,3-dipropyl-3,7-dihydro-purine-2,6-dione; compound with trifluoro-acetic acid 8-(8-Allylamino-bicyclo[3.2.1]oct-3-yl)-1,3-dipropyl-3,7-dihydro-purine-2,6-dione was hydrogenated in MeOH/HOAc in presence of Pd/C under 60 psi of $H_2$ for 8 hrs. Catalyst was filtered and concentrated. The crude product (mixture of two compounds) was purified by HPLC.

Example 46a

1,3-Dipropyl-8-(8-propylamino-bicyclo[3.2.1]oct-3-yl)-3,7-dihydro-purine-2,6-dione; compound with trifluoro-acetic acid. Mass ($ES^+$ 402)

Example 47

[3-(2,6-Dioxo-1,3-dipropyl-2,3,6,7-tetrahydro-1H-purin-8-yl)-bicyclo[3.2.1]oct-8-yl]-acetic acid 2-[3-(2,6-Dioxo-1,3-dipropyl-2,3,6,7-tetrahydro-1H-purin-8-yl)-bicyclo[3.2.1]oct-8-yl]-malonic acid was converted to the product by refluxing in MeOH in the presence of 1N KOH (1 ml) for 2 days. Mass ($ES^+403$).

Example 48

8-(8-Hydroxy-8-methyl-bicyclo[3.2.1]oct-3-yl)-1,3-dipropyl-3,7-dihydro-purine-2,6-dione Trans 8-Oxo-bicyclo[3.2.1]octane-3-carboxylic acid ethyl ester was synthesized followed the procedural written in J. Org. Chem. 1969, Vol. 34, page 1225–1229.

The above ketone (6.55 g, 33 mmol), toluenesulfonic acid monohydrate (0.63 g, 3 mmol), and ethylene glycol (20 ml) in toluene (100 ml) were refluxed using a Dean-Stark trap for the azeotropic elimination of water. After 8 h, the mixture was cooled down and washed with sodium bicarbonate, dried over magnesium sulfate, and concentrated down to get the correspondent ketal as trans isomer (7.26 g crude).

The above trans-ketal was treated with 1N NaOH in methanol at 50° C. overnight. Methanol was evaporated off under vacuum, acidified with 2N HCl (ice cold), and extracted with ethyl acetate. Ethyl acetate was evaporated off to get 6.42 g cis-8-Oxo-bicyclo[3.2.1]octane-3-carboxylic acid with the carbonyl group protected as Ketal form.

The above cis-acid (6.42 g, 30 mmol), 5,6-Diamino-1,3-dipropyl-1H-pyrimidine-2,4-dione, hydrochloride salt (10.34 g, 39 mmol), 5,6-Diamino-1,3-dipropyl-1H-pyrimidine-2,4-dione (7.51 g, 39 mmol), and diethyl isopropylamine (14 ml, 80 mmol) in methylene chloride (200 ml) were stirred at room temperature overnight. The mixture was then washed with 1N HCl, sodium bicarbonate, and brine, and dried over magnesium sulfate, and concentrated down under vacuo. The residue was refluxed in 1N NaOH/isopropanol overnight. The mixture was cooled down, acidified with 3N HCl, extracted with ethyl acetate, and concentrated down. The residue was then treated with 6N HCl/THF at 75° C. for 3 h to get cis 8-(8-Oxo-bicyclo[3.2.1]oct-3-yl)-1,3-dipropyl-3,7-dihydro-purine-2,6-dione as crude. Purification by column chromatography resulted in 4.5 grams of product (yield 40%).

The above ketone (40 mg, 0.11 mmol) was dissolved in THF (7 ml). Methylmagnisium bromide (0.4 ml, 1N in THF) was added to the solution. The reaction mixture was stirred at room temperature for 2 h. The reaction was then quenched with $NH_4Cl$ solution. Column purification resulted in 25 mg title compound (yield 60%). MS (M+1 375).

Example 49

Trans-3-[3-(2,6-Dioxo-1,3-dipropyl-2,3,6,7-tetrahydro-1H-purin-8-yl)-bicyclo[3.2.1]oct-8-yl]-propionic acid (Methoxymethyl)triphenylphosphonium chloride (296 mg 0.86 mmol) in toluene was cooled in an ice-bath. Potassium bis(trimethylsilyl)amide (2.5 ml, 0.5M in toluene) was added dropwise through a syringe. The mixture was stirred at 0° C. for 1 h. 8-(8-Oxo-bicyclo[3.2.1]oct-3-yl)-1,3-dipropyl-3,7-dihydro-purine-2,6-dione (100 mg) was then added to the mixture, and the mixture was allowed to warm to room temperature and was stirred overnight. Toluene was evaporated off, and the residue was treated with 1N HCl in THF at 70° C. for 3 h. Ethyl acetate was used to extract the product. Column chromatography gave 94 mg of 3-(2,6-Dioxo-1,3-dipropyl-2,3,6,7-tetrahydro-1H-purin-8-yl)-bicyclo[3.2.1]octane-8-carbaldehyde as a mixture of cis and trans yield (90%)

The above-obtained aldehyde (300 mg, 0.80 mmol) in THF (10 ml) was reacted with (triphenyl-15-phosphanylidene)-acetic acid methyl ester (540 mg, 1.6 mmol), and the mixture was refluxed for 16 h. Solvent was then evaporated off, Purification by column chromatography resulted in 300 mg of 3-[3-(2,6-Dioxo-1,3-dipropyl-2,3,6,7-tetrahydro-1H-purin-8-yl)-bicyclo[3.2.1]oct-8-yl]-acrylic acid methyl ester as a mixture of cis and trans (Yield 70%).

After hydrogenation in Methanol using 10% Pd/C at 40 psi for 4 h got 3-[3-(2,6-dioxo-1,3-dipropyl-2,3,6,7-tetrahydro-1H-purin-8-yl)-bicyclo[3.2.1]oct-8-yl]-propionic acid methyl ester.

The above methyl ester was hydrolyzed in 1N NaOH/methanol at 60° C. for 30 minutes. Preparative HPLC followed by work up resulted in 19 mg title compound as trans isomer. MS (M+1 417).

Example 43a Cis-3-[3-(2,6-Dioxo-1,3-dipropyl-2,3,6,7-tetrahydro-1H-purin-8-yl)bicyclo[3.2.1]oct-8-yl]-propionic acid The cis isomer (5 mg) obtained from the above experiment was the title compound. MS (M+1 417).

ExampleExample 50

ExampleTrans-3-(2,6-Dioxo-1,3-dipropyl-2,3,6,7-tetrahydro-1H-purin-8-yl)-bicyclo[3.2.1]octane-8-carboxylic acid 3-(2,6-Dioxo-1,3-dipropyl-2,3,6,7-tetrahydro-1H-purin-8-yl)-bicyclo[3.2.1]octane-8-carbaldehyde (94 mg, 0.25 mmol) and 2-methyl-2-butene (2.5 ml, 2.5 mmol) in tert-butanol was stirred at ice-bath. Sodium dihydrogen phosphate monohydrate (348 mg, 2.5 mmol) and sodium chlorite (285 mg, 2.5 mmol) in water was added dropwise. The mixture was gradually brought to room temperature, and was continuously stirred overnight. Ethyl acetate was used to extract the product. Purification from column chromatography resulted in 20 mg title compound as the trans isomer. MS (M+1 389)

ExampleExample 51

ExamplePhosphoric acid mono-[3-(2,6-dioxo-1,3-dipropyl-2,3,6,7-tetrahydro-1H-purin-8-yl)bicyclo[3.2.1]oct-8-yl] ester Followed the procedure for making phosphoric acid mono-[4-(2,6-dioxo-1,3-dipropyl-2,3,6,7-tetrahydro-1H-purin-8-yl)-bicyclo[2.2.2]oct-1-yl] ester (in copending application), the title compound was made by using 8-(8-Hydroxy-bicyclo[3.2.1]oct-3-yl)-1,3-dipropyl-3,7-dihydro-purine-2,6-dione as starting material. Overall yield 70%. MS (M+1 441)

ExampleExample 52

Example{2-[3-(2,6-Dioxo-1,3-dipropyl-2,3,6,7-tetrahydro-1H-purin-8-yl)-bicyclo[3.2.1]oct-8-ylamino]-ethyl}-carbamic acid tert-butyl ester; compound with trifluoro-acetic acid Cis 8-(8-Oxo-bicyclo[3.2.1]oct-3-yl)-1,3-dipropyl-3,7-dihydro-purine-2,6-dione (50 mg, 0.12 mmol), (2-Amino-ethyl)-carbamic acid tert-butyl ester (35 mg, 0.2 mmol), and acetic acid (2 drops) in CH$_2$Cl$_2$/MeOH were stirred for 30 minutes. Sodium cynoborohydride (0.5 ml, 1N in THF) was added to the mixture. The reaction mixture was stirred overnight. The mixture was washed by sodium bicarbonate and brine, and was concentrated down under vacuo. After Prep. HPLC got 10 mg of product as TFA salt. MS (M+1 503).

The following compounds were made in an analogous fashion:

ExampleExample 52a

Example1,3-Dipropyl-8-{8-[(thiophen-2-ylmethyl)-amino]-bicyclo[3.2.1]oct-3-yl}-3,7-dihydro-purine-2,6-dione; compound with trifluoro-acetic acid. MS (M+1 456)

ExampleExample 52b

Example5-Dimethylamino-naphthalene-1-sulfonic acid {2-[3-(2,6-dioxo-1,3-dipropyl-2,3,6,7-tetrahydro-1H-purin-8-yl)-bicyclo[3.2.1]oct-8-ylamino]-ethyl}-amide; compound with trifluoro-acetic acid. MS (M+1 636)

ExampleExample 52c

Example8-{8-[2-(1H-Indol-3-yl)-ethylamino]-bicyclo[3.2.1]oct-3-yl}-1,3-dipropyl-3,7-dihydro-purine-2,6-dione; compound with trifluoro-acetic acid. MS (M+1 503)

ExampleExample 52d

Example8-{8-[2-(5-Nitro-pyridin-2-ylamino)-ethylamino]-bicyclo[3.2.1]oct-3-yl}-1,3-dipropyl-3,7-dihydro-purine-2,6-dione. MS (M+1 525)

ExampleExample 52e

Example1,3-Dipropyl-8-[8-(2-pyridin-2-yl-ethylamino)-bicyclo[3.2.1]oct-3-yl]-3,7-dihydro-purine-2,6-dione. MS (M+1 465).

ExampleExample 52f

ExampleTrifluoro-acetic acid; 8-{8-[2-(2-methyl-5-nitro-imidazol-1-yl)-ethylamino]-bicyclo[3.2.1]oct-3-yl}-1,3-dipropyl-3,7-dihydro-purine-2,6-dione. MS (M+1 513).

ExampleExample 52g

Example(1H-Benzoimidazol-2-ylmethyl)-[3-(2,6-dioxo-1,3-dipropyl-2,3,6,7-tetrahydro-1H-purin-8-yl)-bicyclo[3.2.1]oct-8-yl]-ammonium; trifluoroacetate. MS (M+1 490).

Example 53

(1H-Benzoimidazol-2-ylmethyl)-[3-(2,6-dioxo-1,3-dipropyl-2,3,6,7-tetrahydro-1H-purin-8-yl)-bicyclo[3.2.1]oct-8-ylmethyl]-ammonium; trifluoro-acetate Followed the same reductive amination procedure as described in Example 52. The title compound was synthesized by using 3-(2,6-Dioxo-1,3-dipropyl-2,3,6,7-tetrahydro-1H-purin-8-yl)-bicyclo[3.2.1]octane-8-carbaldehyde and C-(1H-Benzoimidazol-2-yl)methylamine as starting material. MS (M+1 514).

The following compounds were made in an analogous fashion:

Example 53a

[3-(2,6-Dioxo-1,3-dipropyl-2,3,6,7-tetrahydro-1H-purin-8-yl)bicyclo[3.2.1]oct-8-ylmethyl]-(3-imidazol-1-yl-propyl)-ammonium; trifluoro-acetate. MS (M+1 482).

Example 53b (2-tert-Butoxycarbonylamino-ethyl)-[3-(2,6-dioxo-1,3-dipropyl-2,3,6,7-tetrahydro-1H-purin-8-yl)-bicyclo[3.2.1]oct-8-ylmethyl]-ammonium; trifluoro-acetate. MS (M+1 517)

Example 53bc

[3-(2,6-Dioxo-1,3-dipropyl-2,3,6,7-tetrahydro-1H-purin-8-yl)bicyclo[3.2.1]oct-8-ylmethyl]-thiophen-2-ylmethyl-ammonium; trifluoro-acetate. MS (M+1 470)

Example 53d

[2-(5-Dimethylamino-naphthalene-1-sulfonylamino)-ethyl]-[3-(2,6-dioxo-1,3-dipropyl-2,3,6,7-tetrahydro-1H-purin-8-yl)-bicyclo[3.2.1]oct-8-ylmethyl]-ammonium; trifluoro-acetate. MS (M+1 650)

Example 53e

[3-(2,6-Dioxo-1,3-dipropyl-2,3,6,7-tetrahydro-1H-purin-8-yl)bicyclo[3.2.1]oct-8-ylmethyl]-[2-(1H-indol-3-yl)-ethyl]-ammonium; trifluoro-acetate. MS (M+1 517)

Example 53f

[3-(2,6-Dioxo-1,3-dipropyl-2,3,6,7-tetrahydro-1H-purin-8-yl)bicyclo[3.2.1]oct-8-ylmethyl]-[2-(5-nitro-pyridin-2-ylamino)-ethyl]-ammonium; trifluoroacetate. MS (M+1 539)

Example 53g

[3-(2,6-Dioxo-1,3-dipropyl-2,3,6,7-tetrahydro-1H-purin-8-yl)bicyclo[3.2.1]oct-8-ylmethyl]-(2-pyridin-2-yl-ethyl)-ammonium; trifluoro-acetate MS (M+1 479)

Example 53h

[2-(1H-Benzoimidazol-2-yl)-ethyl]-[3-(2,6-dioxo-1,3-dipropyl-2,3,6,7-tetrahydro-1H-purin-8-yl)-bicyclo[3.2.1]oct-8-ylmethyl]-ammonium; trifluoro-acetate MS (M+1 518)

Example 53i

[2-(1H-Benzoimidazol-2-yl)-ethyl]-[3-(2,6-dioxo-1,3-dipropyl-2,3,6,7-tetrahydro-1H-purin-8-yl)-bicyclo[3.2.1]oct-8-yl]-ammonium; trifluoro-acetate MS (M+1 504)

Example 54

8-(3-Oxo-4-aza-tricyclo[3.2.1.0$^{2,7}$]oct-6-yl)-1,3-dipropyl-3,7-dihydro-purine-2,6-dione 8-(5-Oxo-tricyclo[2.2.1.0$^{2,6}$]hept-3-yl)-1,3-dipropyl-3,7-dihydro-purine-2,6-dione (150 mg) was taken in HOAc (5 ml) and H$_2$NOSO$_3$H (100 mg) was added and refluxed for 5 hrs. Cooled to room temperature, treated with ice, sat NaHCO$_3$, extracted with ethyl acetate, washed with brine, and dried over MgSO$_4$. After concentration, the crude product was crystallized from acetone/water. Yield (135 mg). Mass (ES$^+$358).

Example 55

1,3-Dipropyl-7-pyrrolidin-1-ylmethyl-3,7-dihydro-purine-2,6-dione

A solution of 1,3-dipropyl-3,9-dihydro-purine-2,6-dione (446 mg, 1.89 mmol), 37% aqueous formaldehyde (1.2 eq, 2.26 mmol, 0.190 ml) and pyrrolidine (1.2 eq, 2.26 mmol, 161 mg) in EtOH (25 ml) was heated at reflux for 36 h. The cool reaction mixture was concentrated in vacuo to give a solid that was dried in vacuo for 24 h (598 mg, 99%). $^1$H NMR (300 MHz, CDCl$_3$); d 0.94 (coincident t, 6H), 1.64 (m, 2H), 1.75 (m, 4H), 1.78 (m, 2H, partially-obscured), 2.69 (m, 2H), 4.00 (m, 4H), 5.30 (s, 2H), 7.59 (s, 1H); MS: 320 (MH$^+$).

Example 56

8-(3-Hydroxy-8-oxa-bicyclo[3.2.1]oct-6-en-3-yl)-1,3-dipropyl-3,9-dihydro-purine-2,6-dione To a stirred solution of 1,3-dipropyl-7-pyrrolidin-1-ylmethyl-3,7-dihydro-purine-2,6-dione (Example 48) (522 mg, 1.63 mmol) in THF (50 ml) at −78° C. was added n-BuLi (1.55 M in hexanes, 1.2 eq, 1.3 ml). The color of the resulting yellow mixture deepened to orange-red and was stirred at this temperature for 0.5 h. A solution of 8-oxa-bicyclo[3.2.1]oct-6-en-3-one (1.1 eq, 222 mg, 1.79 mmol) in THF (4 ml) was added via syringe over a period of 20 minutes. The mixture was held at −78° C. for 2 h and allowed to reach ambient temperature overnight (12 h). The reaction mixture was partitioned between saturated aqeuous $NH_4Cl$ (20 ml) and EtOAc (20 ml) and the aqueous phase was extracted with EtOAc (20 ml). The combined organic extracts were washed with saturated aqeuous NaCl (20 ml), dried ($MgSO_4$), filtered and concentrated in vacuo. The resulting orange oil was purified by chromatography on silica using 5% MeOH in $CH_2Cl_2$ as eluent to give a clear oil that solidified upon standing (50 mg, 8%).

$^1$H NMR (300 MHz, $CDCl_3$); d 0.94 (coincident t, 6H), 1.66 (m, 2H), 1.77 (m, 2H), 1.83 (d, 2H, J=14.6 Hz), 2.77 (dd, 2H, J=4.0, 14.7 Hz), 3.97 (t, 2H), 4.05 (t, 2H), 4.30 (br s, 1H), 4.91 (d, 2H, J=3.7 Hz), 6.59 (s, 2H); MS: 361 (MH$^+$).

ExampleExample 57

Example8-(8-Oxa-bicyclo[3.2.1]oct-6-en-3-yl)-1,3-dipropyl-3,7-dihydro-purine-2,6-dione To an ice-cold suspension of (methoxymethyl)triphenylphosphonium chloride (1.77 mmol, 0.61 g) in PhMe (6 ml) was added a solution of potassium hexamethyldisilazide (0.5 M, 3.48 ml). The resulting red-orange mixture was stirred at ice temperature for 30 min. To the cold mixture was added 8-oxa-bicyclo[3.2.1]oct-6-en-3-one (Mann, J. et al., *J. Chem. Soc. Perkin Trans I* 1992, 787) (1.61 mmol, 0.200 g) as a solution in PhMe (6 ml). The reaction was stirred overnight with warming to room temperature and then partitioned between saturated $NH_4Cl$ and $Et_2O$. The aqueous was extracted with $Et_2O$ and the combined organic extracts washed with saturated $NH_4Cl$, $H_2O$, and brine and dried ($MgSO_4$). Filtration and evaporation followed by flash column chromatography, eluting with an $Et_2O/CH_2Cl_2$ gradient provided the desired product (0.179 g, 73%) as a yellow liquid. TLC (silica, 1:1 $Et_2O$/hexanes, $I_2$ visualization)$R_f$ (desired product)=0.59

To a solution of 3-methoxymethylene-8-oxa-bicyclo [3.2.1]oct-6-ene (1.18 mmol, 0.18 g) in THF (1.2 ml) was added at room temperature 1N HCl (1.2 ml). The reaction was stirred overnight at room temperature, then quenched with 5% $NaHCO_3$ and extracted with $Et_2O$. The combined organic extracts were washed with 5% $NaHCO_3$, brine and dried ($MgSO_4$). Filtration and evaporation provided the title compound (0.155 g, 95%) as an oil. TLC(silica, 1:1 $Et_2O$/hexanes, $I_2$ visualization)Rf(desired product)=0.22

To a solution of 8-oxa-bicyclo[3.2.1]oct-6-ene-3-carbaldehyde (0.434 mmol, 0.060 g) in EtOH (2.2 ml) at room temperature was added 1N NaOH (2.2 ml) followed by $Ag_2O$ (0.521 mmol, 0.121 g). The reaction, which became slightly warm, was stirred briskly 1 h. The mixture was filtered on a pad of Celite, rinsing the flask and cake with 1:1 $EtOH/H_2O$. The filtrate was concentrated to remove the bulk of the EtOH and the aqueous residue extracted with $Et_2O$. These extracts were discarded. The aqueous phase was acidified (pH 4) with conc. HCl and extracted with $Et_2O$. These extracts were washed with brine and dried ($MgSO_4$). Filtration and evaporation provided the desired product (0.0386 g, 58%) as an oil that solidified on standing. By $^1$H NMR analysis, the endo isomer was not detected. $^1$H NMR (300 MHz, $CDCl_3$): 1.67 (br dd, 2H, J=5.88, 13.7 Hz), 1.92 (ddd, 2H, J=3.62, 11.6, 13.7 Hz), 2.80 (tt, 1H, J=5.88, 11.6 Hz), 4.78 (br s, 2H), 6.16 (s, 2H).

To a solution of 8-oxa-bicyclo[3.2.1]oct-6-ene-3-carboxylic acid (0.25 mmol, 0.0386 g), HATU (0.25 mmol, 0.0952 g), and 5,6-diamino-1,3-dipropyl-1H-pyrimidine-2,4-dione hydrochloride (Daly, J. W. et al., *J. Med. Chem.*, 1985, 28 (4), 487) (0.25 mmol, 0.0658 g) in DMF (2.5 ml) was added iPr$_2$NEt (0.75 mmol, 0.13 ml). The reaction was stirred overnight at room temperature. It was concentrated at the pump to remove DMF. The residue was dissolved in EtOAc and washed with 1N HCl, 5% $NaHCO_3$, and brine and dried ($MgSO_4$). Filtration and evaporation followed by flash column chromatography, eluting with a $THF/CH_2Cl_2$ gradient provided the desired product (0.067 g, 74%) as an oil that solidified on standing. $^1$H NMR (300 MHz, $CDCl_3$): 0.90 (t, 3H, J=7.4 Hz), 0.97 (t, 3H, J=7.3 Hz), 1.53–1.72 (m, 6H), 1.95–2.03 (m, 2H), 3.0 (br m, 1H), 3.82–3.91 (m, 4H), 4.79 (br s, 2H), 6.18 (s, 2H).

A solution of 8-oxa-bicyclo[3.2.1]oct-6-ene-3-carboxylic acid (6-amino-2,4-dioxo-1,3-dipropyl-1,2,3,4-tetrahydro-pyrimidin-5-yl)-amide (0.185 mmol, 0.067 g) in 20% NaOH (1.23 ml) and MeOH (6.2 ml) was stirred and refluxed overnight. The reaction was cooled to room temperature and then concentrated to remove MeOH. The aqueous residue was extracted with $Et_2O$ and these extracts discarded. The aqueous was acidified (pH 2–3) with conc. HCl and then extracted with EtOAc. The combined EtOAc extracts were washed with $H_2O$ and brine and dried ($MgSO_4$). Filtration and evaporation followed by flash column chromatography, eluting with 1:1 EtOAc/$CH_2Cl_2$, provided the title compound (0.037 g, 58%) as a beige solid. $^1$H NMR (300 MHz, $CDCl_3$): 0.93–0.99 (m, 6H), 1.62–1.83 (m, 6H), 2.14–2.25 (m, 2H), 3.40–3.51 (m, 1H), 4.05–1.10 (m, 4H), 4.86 (br s, 2H), 6.25 (s, 2H).

ExampleExample 58

Example8-(8-Oxa-bicyclo[3.2.1]oct-3-yl)-1,3-dipropyl-3,7-dihydro-purine-2,6-dione To a solution of 8-(8-Oxa-bicyclo[3.2.1]oct-6-en-3-yl)-1,3-dipropyl-3,7-dihydro-purine-2,6-dione (Example 50) (0.029 mmol, 0.010 g) in MeOH (5 ml) was added 10% Pd/C (50% $H_2O$) and the resulting suspension stirred briskly under $H_2$ (1 atm) for 2 h. The mixture was filtered through Celite and the cake rinsed with MeOH. Filtration and evaporation followed by purification by PLC, eluting with 1:1 EtOAc/$CH_2Cl_2$, provided the title compound (0.010 g, 100%). $^1$H NMR (100 MHz, $CDCl_3$): 0.93–0.99 (m, 6H), 1.68–1.89 (m, 8H), 2.04–2.07 (m, 2H), 2.16–2.25 (m, 2H), 3.34–3.42 (m, 1H), 4.05–4.12 (m, 4H), 4.50 (br s, 2H), 8.9 (br s, 1H).

ExampleExample 59

Example1,3-Dipropyl-7-(tetrahydro-pyran-2-yl)-3,7-dihydro-purine-2,6-dione

A suspension of 1,3-dipropyl-3,9-dihydro-purine-2,6-dione (1.0 g, 4.2 mmol) and PPTS (0.42 mmol, 106 mg) in 3,4-dihydropyran (15 ml) and $CHCl_3$ (5 ml) was stirred at room temperature for 48 h. The solvent was removed in vacuo to give a pale yellow solid that was dissolved in CH$_2$Cl$_2$, washed with water (2×20 ml), dried (Na$_2$SO$_4$), filtered and concentrated in vacuo to give a white solid (1.2 g, 89%). MS: 343 (MH$^+$).

ExampleExample 60

Example3-(2,6-Dioxo-1,3-dipropyl-2,3,6,7-tetrahydro-1H-purin-8-yl)-3-hydroxy-8-oxa-bicyclo[3.2.1]octane-6,7-dicarboxylic acid dimethyl ester A solution of LDA was prepared at –78° C. by addition of n-BuLi (1.8 M in hexanes, 1.7 ml) to a solution of iPr$_2$NH (3.61 mmol, 0.506 ml) in THF (25 ml). After addition, the LDA was aged at –78° C. for 45 min. To this was added slowly at –78° C. a solution of 1,3-dipropyl-7-(tetrahydropyran-2-yl)-3,7-dihydropurine-2,6-dione (Example 52) (2.78 mmol, 0.89 g) in THF (35 ml). After stirring another 1 h at –78° C., a solution of 8-oxa-bicyclo[3.2.1]oct-6-en-3-one (Mann, J. et al., *J. Chem. Soc. Perkin Trans I* 1992, 787) (2.78 mmol, 0.345 g) in THF (5 ml) was added. The reaction was stirred overnight with warming to room temperature. It was quenched by addition of saturated NH$_4$Cl and extracted with EtOAc. The combined organic extracts were washed with saturated NH$_4$Cl, H$_2$O and brine, and dried (MgSO$_4$). Filtration and evaporation followed by flash column chromatography, eluting with an EtOAc/CH$_2$Cl$_2$ gradient, provided the desired product (0.55 g, 45%). MS (ESP+, 60V): 445.07 (M+H, 35%), 361.06 (48%), 343.05 (100%).

A solution of 8-(3-hydroxy-8-oxa-bicyclo[3.2.1]oct-6-en-3-yl)-1,3-dipropyl-7-(tetrahydropyran-2-yl)-3,7-dihydropurine-2,6-dione (0.113 mmol, 0.050 g) and Et$_3$N (1.13 mmol, 0.16 ml) in MeOH (3 ml) was saturated with CO bubbled in from a lecture bottle over 30 min. To the reaction was then added PdCl$_2$ (0.023 mmol, 0.0041 g) and CuCl$_2$ (0.339 mmol, 0.046 g). The reaction was stirred overnight at room temperature under a static atmosphere of CO. The completed reaction was quenched by the addition of concentrated NH$_4$OH, diluted with EtOAc and filtered through Celite to remove solids. The biphasic filtrate was separated and the aqueous extracted with EtOAc. The combined organics were washed with 1N HCl, saturated NaHCO$_3$, H$_2$O and brine, and dried (MgSO$_4$). Filtration and evaporation provided the desired product (0.060 g, 94%). MS (ESP+, 60V): 563.13 (M+H, 28%), 479.10 (100%).

To a solution of 3-[2,6-dioxo-1,3-dipropyl-7-(tetrahydropyran-2-yl)-2,3,6,7-tetrahydro-1H-purin-8-yl]-3-hydroxy-8-oxa-bicyclo[3.2.1]octane-6,7-dicarboxylic acid dimethyl ester (0.060 mmol, 0.030 g) in 1:1 THF/MeOH (6 ml) was added 1N HCl (3 drops). The reaction was stirred at room temperature 3d and then concentrated to dryness. The residue was purified by PLC on a 1 mm layer, eluting with 20% THF/CH$_2$Cl$_2$, providing the title compound (0.0162 g, 56%). $^{13}$C NMR (100 MHz, CDCl$_3$): 11.53 (q), 11.50 (q), 21.72 (t), 21.75 (t), 41.74 (t), 43.82 (t), 45.85 (t), 51.02 (d), 52.64 (q), 70.37 (s), 77.12 (d), 107.53 (s), 149.12 (s), 151.17 (s), 156.32 (s), 159.98 (s), 173.36 (s).

ExampleExample 61

Example8-(3-Hydroxy-6,7-bis-hydroxymethyl-8-oxa-bicyclo[3.2.1]oct-3-yl)-1,3-dipropyl-3,7-dihydropurine-2,6-dione To a solution of 3-[2,6-dioxo-1,3-dipropyl-7-(tetrahydropyran-2-yl)-2,3,6,7-tetrahydro-1H-purin-8-yl]-3-hydroxy-8-oxa-bicyclo[3.2.1]octane-6,7-dicarboxylic acid dimethyl ester (Example 53) (0.060 mmol, 0.030 g) in THF (3 ml) was added a solution of LiBH$_4$ (2M, 0.050 ml). The reaction was stirred at room temperature 3d. It was then carefully quenched by addition of 1N HCl and extracted with EtOAc. The combined organic extracts were washed with saturated NaHCO$_3$ (1X) and brine, and dried (MgSO$_4$). Filtration and evaporation provided the desired product (0.028 g, 92%) as an oil. MS (ESP+, 60V): 529.7 (M+Na, 20%), 507.32 (M+H, 43%), 423.20 (87%), 223.08 (100%).

To a solution of 8-(3-hydroxy-6,7-bis-hydroxymethyl-8-oxa-bicyclo[3.2.1]oct-3-yl)-1,3-dipropyl-7-(tetrahydropyran-2-yl)-3,7-dihydropurin-(2,6-dione 0.059 mmol, 0.030 g) in 1:1 THF/MeOH (6 ml) was added 1N HCl (0.5 ml). The reaction was stirred at room temperature overnight and then concentrated to dryness. The residue was purified by reverse phase HPLC, providing the title compound (0.0024 g, 10%). MS (ESP+, 60V): 423.15 (M+H, 100%);MS (ESP-, 60V): 421.01(M–H, 100%).

ExampleExample 62

Example4-(2,6-Dioxo-1,3-dipropyl-2,3,6,7-tetrahydro-1H-purin-8-yl)-bicyclo-[3.2.1]octane-1-carboxylic acid Using the procedure described in Example 50, 4-oxo-bicyclo[3.2.1]octane-1-carboxylic acid ethyl ester (Kraus, W., et al. *Liebigs Ann. Chem.* 1981, 10, 1826; Kraus, W., et al. *Tetrahedron Lett.* 1978, 445; Filippini, M.-H. et al. *J. Org. Chem.* 1995, 60, 6872) (6.17 mmol, 1.21 g) was converted to the desired product. Flash chromatography, eluting with 10% Et$_2$O/hexanes provided pure product (0.96 g, 69%) as a liquid (mixture of E/Z isomers). $^{13}$C NMR (100 MHz, CDCl$_3$): 14.31 (q), 19.15 (t), 22.97 (t), 23.61 (t), 23.91 (t), 29.97 (t), 31.13 (t), 32.04 (t), 32.36 (t), 34.61 (t), 34.85 (d), 35.81 (t), 43.18 (t), 43.63 (t), 50.47 (s), 50.77 (s), 59.63 (q), 59.69 (t), 121.04 (s), 121.44 (s), 137.18 (d), 138.16 (d), 177.60 (s), 177.63 (s).

Using the procedure described in Example 50, 4-methoxymethylene-bicyclo[3.2.1]octane-1-carboxylic acid ethyl ester (3.84 mmol, 0.86 g) was converted to the desired product (0.81 g, 100%). TLC(silica, 20% Et$_2$O/hexanes, 20% PMA/EtOH visualization) R$_f$ (desired product) =0.29.

To an ice-cold solution of 4-formyl-bicyclo[3.2.1]octane-1-carboxylic acid ethyl ester (3.85 mmol, 0.81 g) was added slowly Jones reagent (2.7 M, 1.43 ml). The reaction was stirred at ice temperature 20 min, then quenched by addition of iPrOH, diluted with H$_2$O and extracted with Et$_2$O. The combined organic extracts were washed with H$_2$O, brine, and dried (MgSO$_4$). Filtration and evaporation provided the viscous oily desired product (0.76 g, 87%) as a mixture of axial and equatorial acids. $^{13}$C NMR (100 MHz, CDCl$_3$): 14.16 (q), 19.86 (t), 21.07 (t), 25.98 (t), 29.20 (t), 31.52 (t), 31.87 (t), 32.27 (t), 33.39 (t), 37.80 (d), 38.07 (t), 38.10 (d), 42.06 (t), 44.80 (d), 45.78 (d), 49.38 (s), 49.60 (s), 60.31 (t), 60.36 (t), 177.08 (s), 180.01 (s).

Using the procedure described in Example 50, Step D, bicyclo[3.2.1]octane-1,4-dicarboxylic acid 1-ethyl ester (0.84 mmol, 0.19 g) was reacted with 5,6-diamino-1,3-dipropyl-1H-pyrimidine-2,4-dione hydrochloride (0.84 mmol, 0.22 g) to provide the desired product (0.36 g, 100%) as a mixture of axial and equatorial amides. MS (ESP+, 60V): 456.95 (M+Na, 45%), 435.00 (M+H, 8%), 325.12 (42%), 280.05 (100%).

Using the procedure described in Example 50, 4-(6-amino-2,4-dioxo-1,3-dipropyl-1,2,3,4-tetrahydro-pyrimidin-5-ylcarbamoyl)-bicyclo[3.2.1]octane-1-carboxylic acid ethyl ester (0.84 mmol, 0.36 g) was converted to the title compound. Flash chromatography eluting with 95:5:0.1 $CH_2Cl_2$/THF/AcOH provided partial separation of the axial (first band, 0.032 g) and equatorial (second band, 0.055 g) isomers. MS (ESP+, 60V): (axial isomer) 389.12 (M+H, 100%), 343.11 (15%); (equatorial isomer) 389.12 (M+H, 100%), 347.05 (8%)

ExampleExample 63

Example4-(2,6-Dioxo-1,3-dipropyl-2,3,6,7-tetrahydro-1H-purin-8-yl)-bicyclo-[3.2.1]oct-3-ene-1-carboxylic acid To a solution of 4-oxo-bicyclo[3.2.1]octane-1-carboxylic acid ethyl ester (Kraus, W., et al. *Liebigs Ann. Chem.* 1981, 10, 1826; Kraus, W., et al. *Tetrahedron Lett.* 1978, 445; Filippini, M.-H. et al. *J. Org. Chem.* 1995, 60, 6872) (0.51 mmol, 0.100 g) in THF (2.5 ml) at −78° C. was added LiHMDS (1.0 M in THF, 0.56 ml). After 1 h at −78° C., a solution of $PhNTf_2$ (0.56 mmol, 0.200 g) in THF (1 ml) was added. The reaction was stirred overnight with warming to room temperature. The completed reaction was concentrated to dryness and the residue purified by passage through a pad of silica gel, eluting with $EtOAc/CH_2Cl_2$. Evaporation of the filtrate provide the desired product (0.15 g, 90%).

A solution of 4-trifluoromethanesulfonyloxy-bicyclo[3.2.1]oct-3-ene-1-carboxylic acid ethyl ester (0.46 mmol, 0.15 g), 5,6-diamino-1,3-dipropyl-1H-pyrimidine-2,4-dione hydrochloride (0.55 mmol, 0.146 g), $iPr_2NEt$ (0.92 mmol, 0.16 ml), $Pd(OAc)_2$ (0.02 mmol, 0.0046 g) and $Ph_3P$ (0.035 mmol, 0.0092 g) in DMF (5 ml) was saturated with CO bubbled in from a lecture bottle over 30 min. The reaction was then stirred and heated 6 h at 100° C. under a static atmosphere of CO. The DMF was removed at the pump. The residue was dissolved in EtOAc, washed with 1N HCl, saturated $NaHCO_3$, $H_2O$, and brine and dried (MgSO4). Filtration and evaporation followed by flash chromatography, eluting with 10% $THF/CH_2Cl_2$ provided pure desired product (0.054 g, 27%) as an oil. MS (ESP+, 60V): 455.16 (M+Na, 13%), 433.1 (M+H, 15%), 439.15 (27%), 182.93 (100%).

Using the procedure described in Example 50, 4-(6-amino-2,4-dioxo-1,3-dipropyl-1,2,3,4-tetrahydro-pyrimidin-5-ylcarbamoyl)-bicyclo[3.2.1]oct-3-1-carboxylic acid ethyl ester (0.125 mmol, 0.054 g) was converted to the title compound. Pure material (0.0031 g, 6.5%) was obtained by reverse phase HPLC. MS (ESP+, 60V): 387.06 (M+H, 100%).

ExampleExample 64

Example1,3-Dipropyl-7-(tetrahydro-pyran-2-yl)-3,7-dihydro-purine-2,6-dione

A suspension of 1,3-dipropyl-3,9-dihydro-purine-2,6-dione (1.0 g, 4.2 mmol) and PPTS (0.42 mmol, 106 mg) in 3,4-dihydropyran (15 ml) and $CHCl_3$ (5 ml) was stirred at room temperature for 48 h. The solvent was removed in vacuo to give a pale yellow solid that was dissolved in $CH_2Cl_2$, washed with water (2×20 ml), dried ($Na_2SO_4$), filtered and concentrated in vacuo to give a white solid (1.2 g, 89%). MS: 343 (MH+).

ExampleExample 65

Figure 1B:
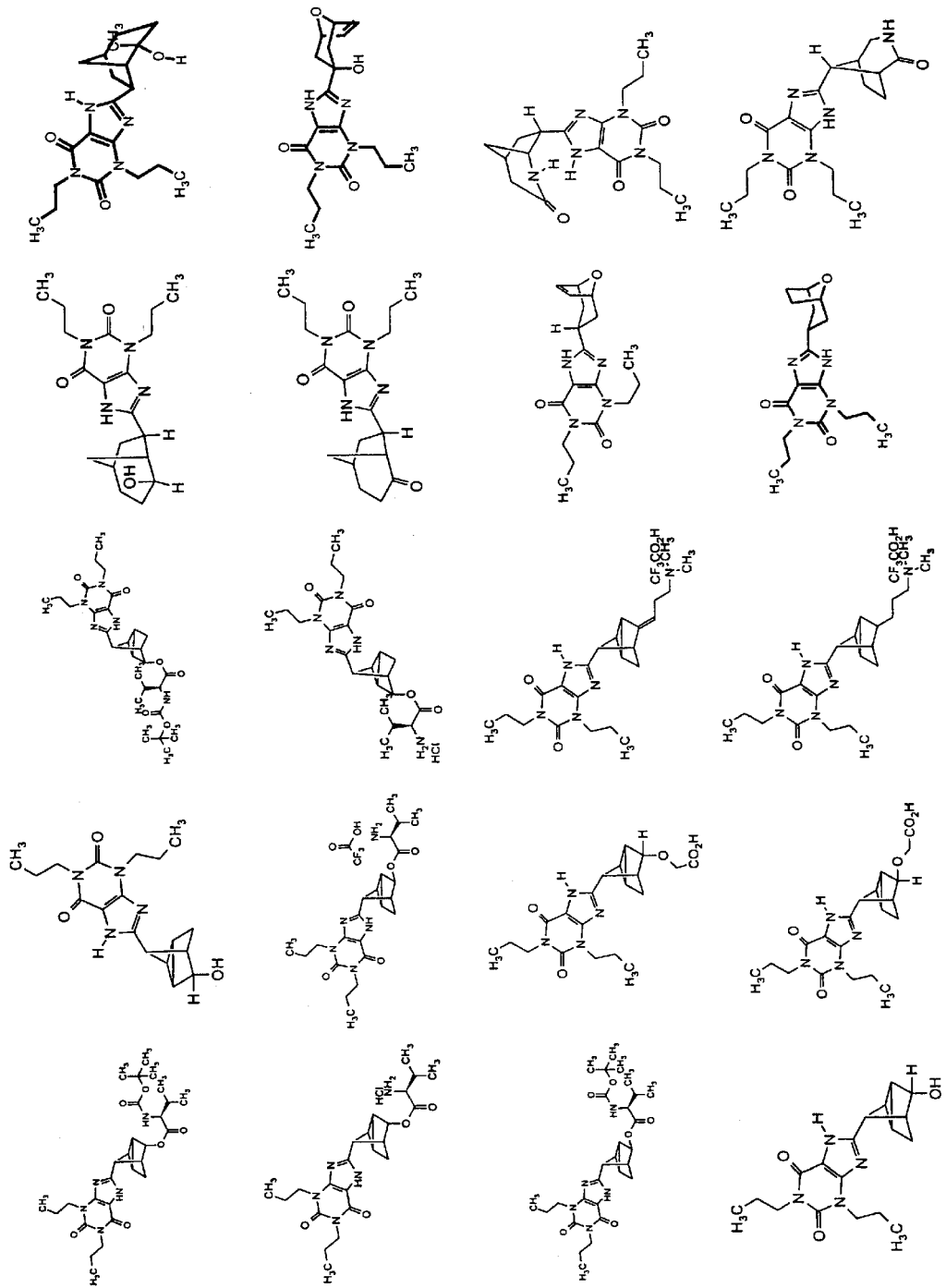
Figure 1C:
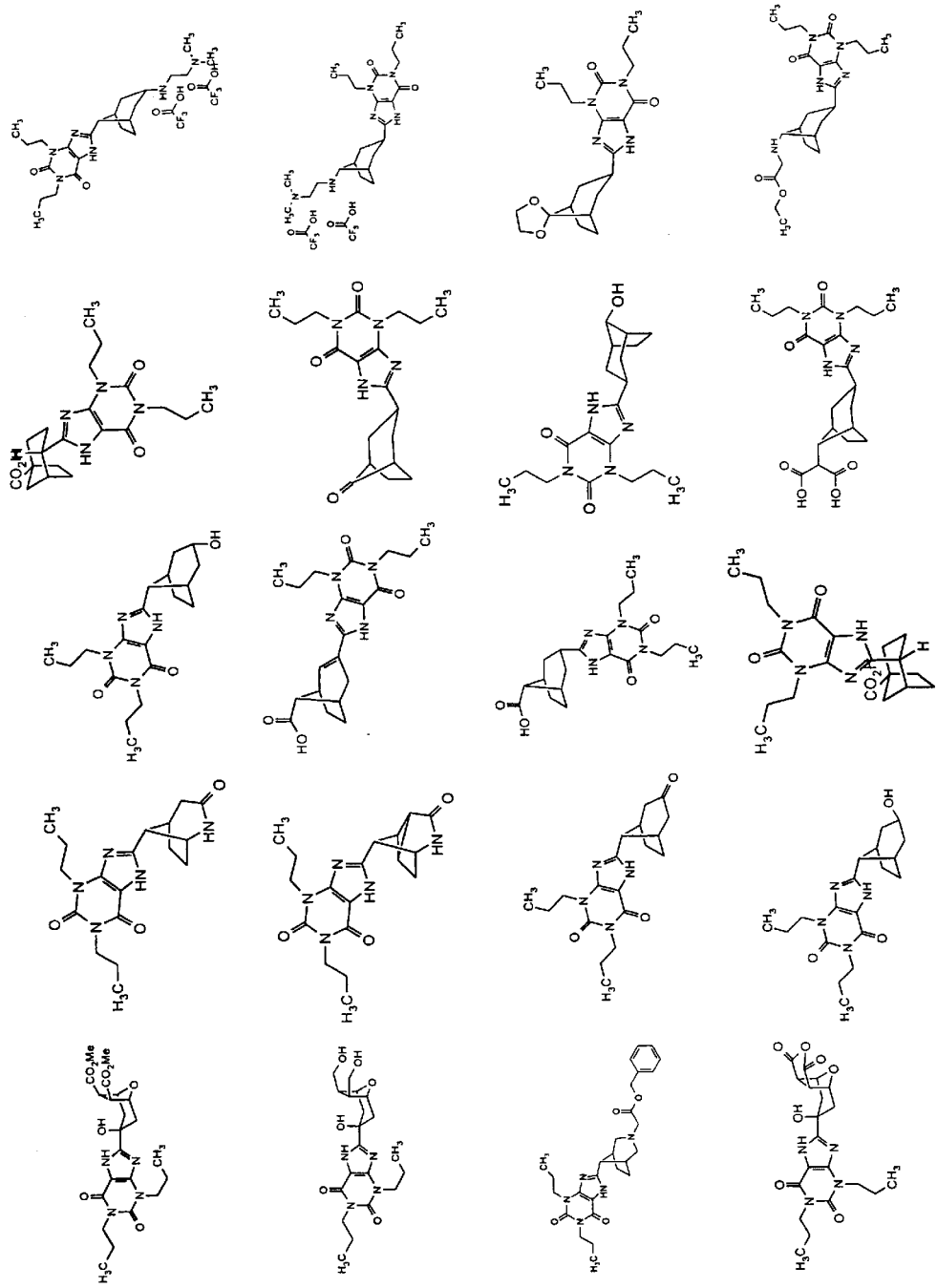
Figure 1D:
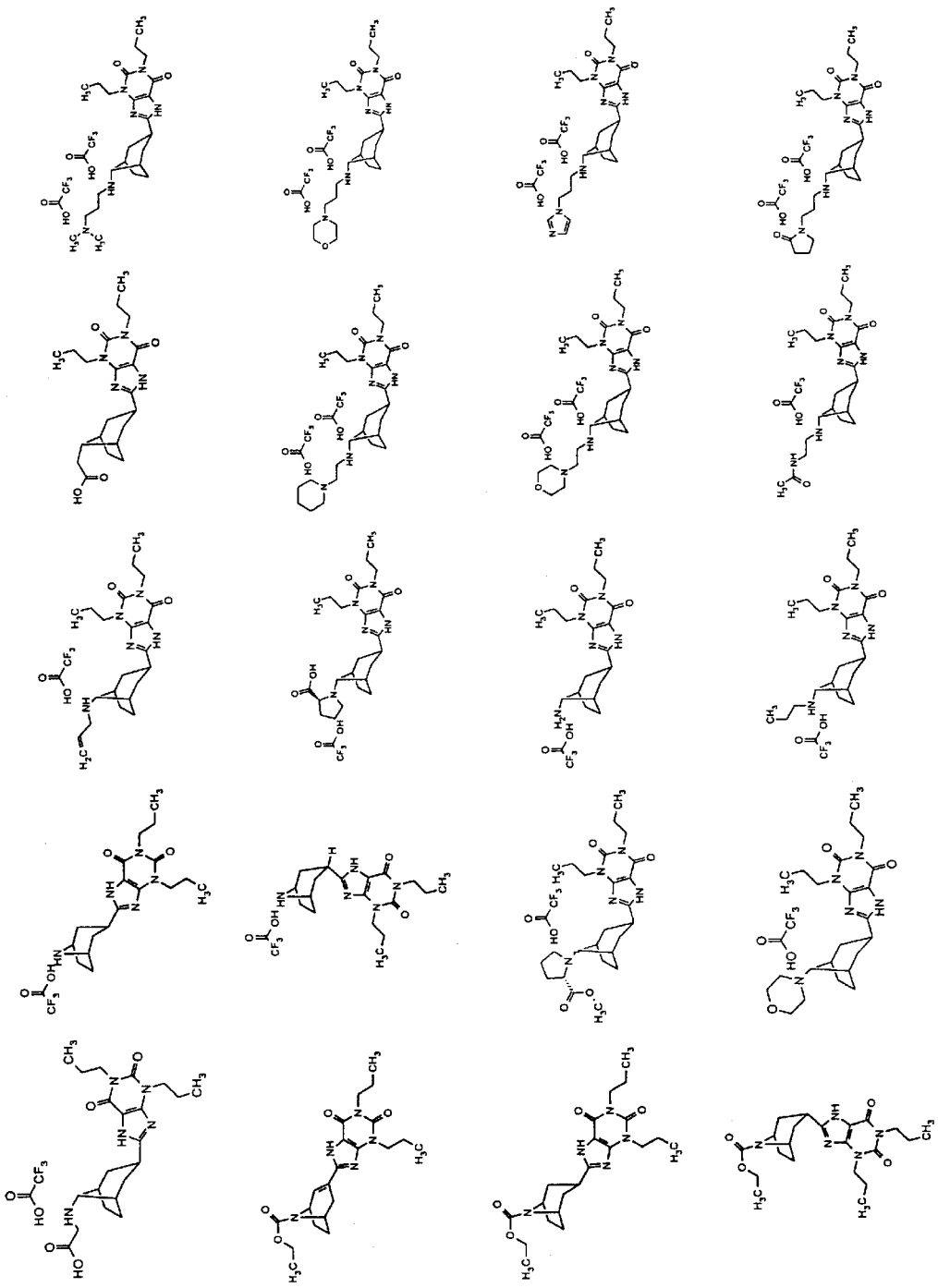
Figure 1E:
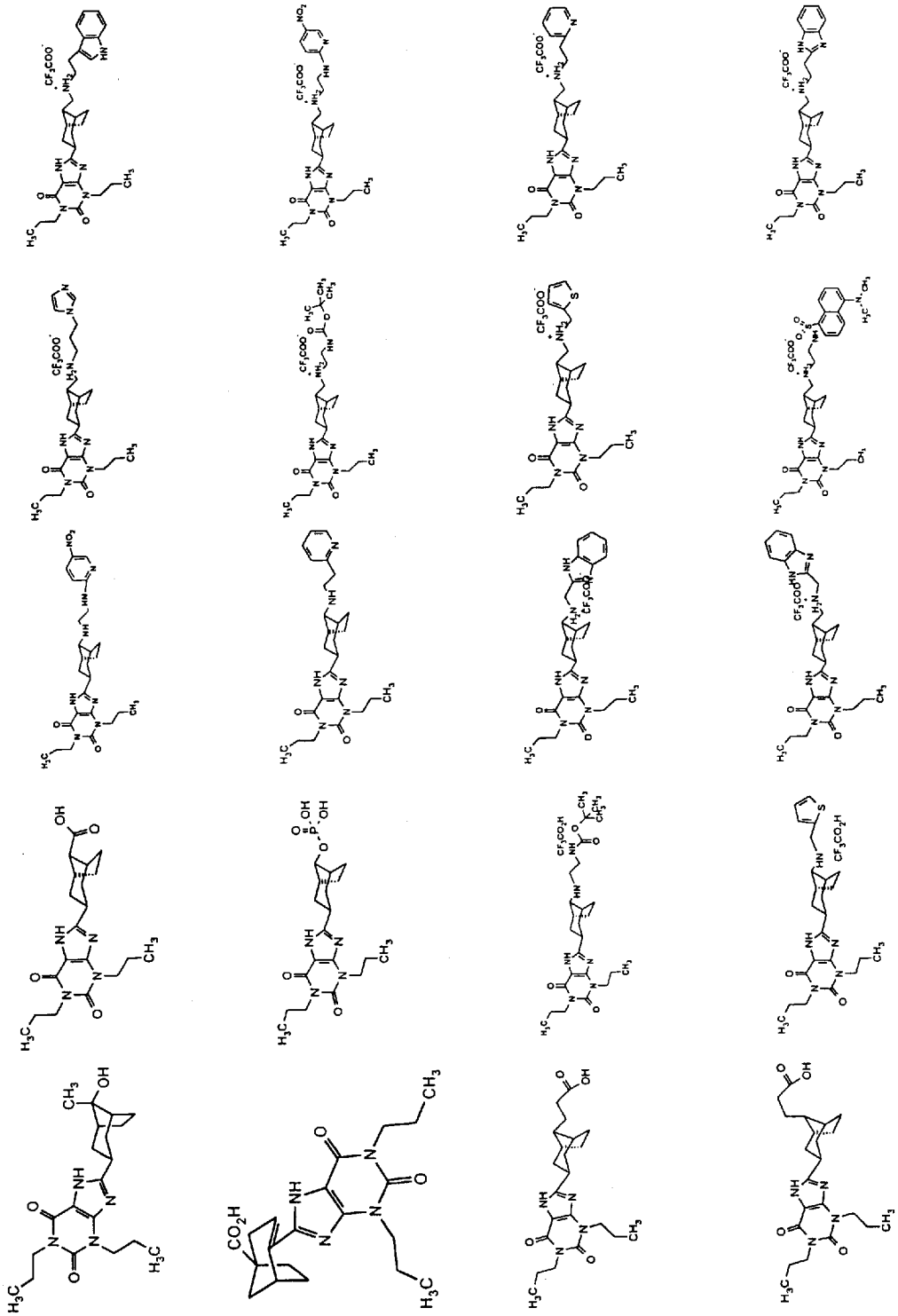
Figure 1F:
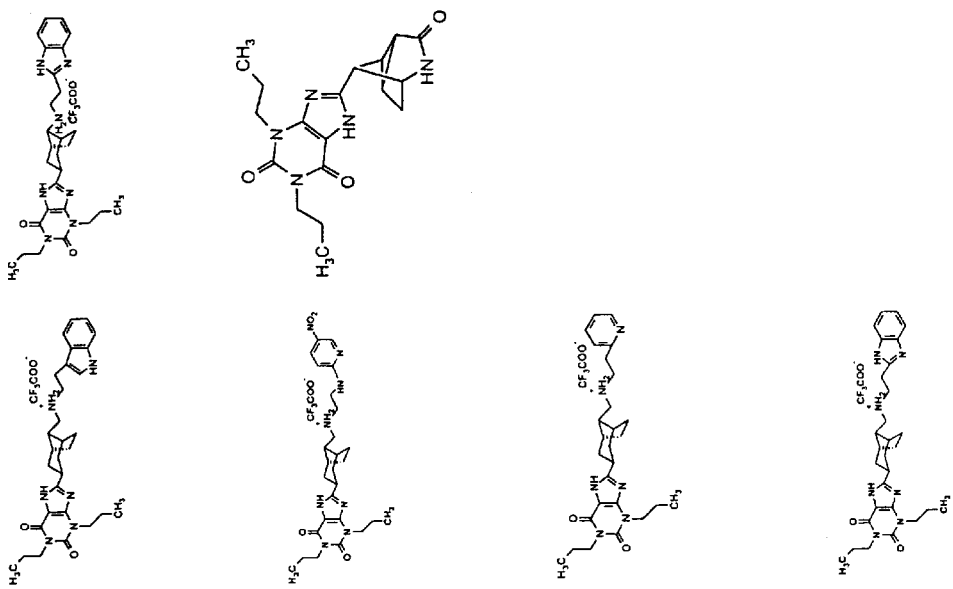

106 xanthine derivatives were prepared, having the structures indicated in FIG. 1. For some of these compounds, the $K_i$ values for rat and human adenosine $A_1$ receptors and for human adenosine $A_{2a}$ receptors were determined according to the following binding assay protocol. The ratio $A_{2a}/A_1$ was also calculated.

Materials

Adenosine deaminase and HEPES were purchased from Sigma (St. Louis, Mo.). Ham's F-12 cell culture medium and fetal bovine serum were purchased from GIBCO Life Technologies (Gaithersburg, Md.). Antibiotic G-418, Falcon 150-mM culture plates and Costar 12-well culture plates were purchased from Fisher (Pittsburgh, Pa.). [$^3$H]CPX was purchased from DuPont-New England Nuclear Research Products (Boston, Mass.). Penicillin/streptomycin antibiotic mixture was purchased from Mediatech (Washington, DC). The composition of HEPES-buffered Hank's solution was: 130 mM NaCl, 5.0 mM Cl, 1.5 mM $CaCl_2$, 0.41 mM $MgSO_4$, 0.49 mM $Na_2HPO_4$, 0.44 mM $KH_2PO_4$, 5.6 mM dextrose, and 5 mM HEPES (pH 7.4).

Membrane Preparation

Rat $A_1$ Receptor: Membranes were prepared from rat cerebral cortex isolated from freshly euthanized rats. Tissues were homogenized in buffer A (10 mM EDTA, 10 mM Na-HEPES, pH 7.4) supplemented with protease inhibitors (10 µg/ml benzamidine, 100 µM PMSF, and 2 µg/ml each of aprotinin, pepstatin and leupeptin), and centrifuged at 20,000×g for 20 min. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Human $A_1$ Receptor: Human A1 adenosine receptor cDNA was obtained by RT-PCR and subcloned into pcDNA3.1(Invitrogen). Stable transfection of CHO-K1 cells was performed using LIPOFECTAMINE-PLUS (GIBCO-BRL) and colonies were selected in 1 mg/ml G418, and screened using radioligand binding assays. For membrane preparations, CHO-K1 cells growing as monolayers in complete media (F12+10%FCS+1 mg/ml G418) were washed in PBS and harvested in buffer A supplemented with protease inhibitors. Cells were homogenized, centrifuged, and washed twice with buffer HE as described above. Final pellets were stored in aliquots at −80° C.

Radioligand Binding Assays

Membranes (50 µg membrane protein for rat A1ARs, and 25 µg of CHO-K1 membrane protein for human A1ARs), radioligands and varying concentrations of competing ligands were incubated in triplicates in 0.1 ml buffer HE plus 2 units/ml adenosine deaminase for 2.5 h at 21° C. Radioligand [$^3$H]DPCPX (112 Ci/mmol from NEN, final concentration:1 nM) was used for competition binding assays on $A_1$ARs. Nonspecific binding was measured in the presence of 10 µM BG9719. Binding assays were terminated by filtration over Whatman GF/C glass fiber filters using a BRANDEL cell harvester. Filters were rinsed three times with 3–4 ml ice-cold 10 mM Tris-HCl, pH 7.4 and 5 mM $MgCl_2$ at 4° C. Filter paper was transferred to a vial, and 3 ml of scintillation cocktail ScintiVerseII (Fisher) was added. Radioactivity was counted in a Wallac β-counter.

Analysis of Binding Data

For $K_I$ Determinations: Competition binding data were fit to a single-site binding model and plotted using Prizm GraphPad. Cheng-Prusoff equation $K_I=IC_{50}/(1+[I]/K_D)$ was used to calculate $K_I$ values from $IC_{50}$ values, where $K_I$ is the affinity constant for the competing ligand, [I] is the concentration of the free radioligand, and $K_D$ is the affinity constant for the radioligand.

For % Binding: For one-point binding assays, data were presented as % of total specific binding at 1 $\mu$M of competing compound: % of total=100* (Specific binding with 1 $\mu$M of competing compound/total specific binding).

Results

All of the compounds tested exhibited rat $A_1$ $K_i$ values between 0.47 and 1225 nM, human $A_1$ $K_i$ values between 12 and 1000 nM, and human $A_{2a}$ $K_i$ values between 18 and 100,000 nM. All of the compounds but one had $A_{2a}/A_1$ ratios of at least 8, most greater than 50, a substantial number greater than 100, and at least one greater than 200.

Example 66

Alternative Assay Methodology

Materials

See Example 65.

Cell Culture

CHO cells stably expressing the recombinant human $A_1$AdoR (CHO:$A_1$AdoR cells) were prepared as described (Kollias-Barker et al., J. Pharma. Exp. Ther. 281(2), 761, 1997) and cultured as for CHO:Wild cells. CHO cells were cultured as monolayers on plastic dishes in Ham's F-12 medium supplemented with 10% fetal bovine serum, 100 U penicillin G and 100 $\mu$g streptomycin in a humidified atmosphere of 5% $CO_2$/95% air at 37° C. The density of [$^3$H]CPX binding sites in CHO cells was 26±2 (n=4) fmol/mg protein. Cells were subcultured twice weekly after detachment using 1 mM EDTA in $Ca^{2+}$-$Mg^{2+}$-free HEPES-buffered Hank's solution. Three different clones of CHO:$A_1$AdoR cells were used for experiments, and all results were confirmed with cells from two or three clones. The density of $A_1$AdoRs in these cells was 4000–8000 fmol/mg protein, as determined by assay of [$^3$H]CPX specific binding.

Radioligand Binding

CHO cells grown on 150 mm culture dishes were rinsed with HEPES-buffered Hank's solution, then removed with a cell scraper and homogenized in ice-cold 50 mM Tris-HCl, pH 7.4. Cell membranes were pelleted by centrifugation of the cell homogenate at 48,000×g for 15 minutes. The membrane pellet was washed twice by resuspension in fresh buffer and centrifugation. The final pellet was resuspended in a small volume of 50 mM Tris-HCl, pH 7.4, and stored in aliquots of 1 ml at −80° C. until used for assays.

To determine the density of $A_1$AdoRs in CHO cell membranes, 100 $\mu$l aliquots of membranes (5 $\mu$g protein) were incubated for 2 hours at 25° C. with 0.15–20 nM [$^3$H]CPX and adenosine deaminase (2 U/ml) in 100 $\mu$l of 50 mM Tris-HCl, pH 7.4. Incubations were terminated by dilution with 4 ml of ice-cold 50 mM Tris-HCl buffer and immediate collection of membranes onto glass-fiber filters (Schleicher and Schuell, Keene, N.H.) by vacuum filtration (Brandel, Gaithersburg, Md.). Filters were washed quickly three times with ice-cold buffer to remove unbound radioligand. Filter discs containing trapped membranes bound radioligand were placed in 4 ml of Scintiverse BD (Fisher), and the radioactivity was quantified using a liquid scintillation counter. To determine nonspecific binding of [$^3$H]CPX, membranes were incubated as described above and 10 $\mu$M CPT was added to the incubation buffer. Nonspecific binding was defined as [$^3$H]CPX bound in the presence of 10 $\mu$M CPT. Specific binding of the radioligand to the $A_1$AdoR was determined by subtracting nonspecific binding from total binding. Nonspecific binding was found to increase linearly with an increase of [$^3$H]CPX concentration. Triplicate assays were done at each tested concentration of [$^3$H]CPX.

To determine the affinities of antagonists of $A_1$AdoRs for the human recombinant $A_1$AdoR expressed in CHO cells, binding of 2 nM [$^3$H]CPX in the presence of increasing concentrations of antagonist was measured. Aliquots of CHO cell membranes (100 $\mu$l: 5 $\mu$g protein), [$^3$H]CPX, antagonist (0.1 nM–100 $\mu$M), and adenosine deaminase (2 U/ml) were incubated for 3 hours at 25° C. in 200 $\mu$l of 50 mM Tris-HCl buffer (pH 7.4). Assays were terminated as described above.

Data Analysis

Binding parameters (i.e., $B_{max}$, $K_d$, $IC_{50}$, $K_i$, and Hill coefficients) were determined using the radioligand binding analysis program LIGAND 4.0 (Elsevier-Biosoft). Most of the compounds tested exhibited $A_{2a}/A_1$ ratios of at least 20, a substantial number were greater than 50, and some were greater than 100.

ExampleOTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising the formula:

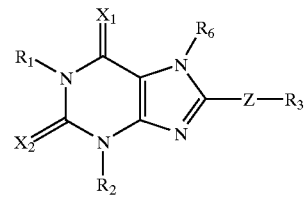

or a pharmacologically acceptable addition salt thereof; wherein $R_1$ and $R_2$, independently, are selected from the group consisting of:
  a) hydrogen;
  b) alkyl, alkenyl of not less than 3 carbons, and alkynyl of not less than 3 carbons; wherein the alkyl, alkenyl, or alkynyl is either unsubstituted or substituted with one or two substituents selected from the group consisting of hydroxy, alkoxy, amino, alkylamino, dialkylamino, heterocyclyl, acylamino, alkylsulfonylamino, and heterocyclylcarbonylamino; and
  c) aryl and substituted aryl;

$R_3$ is a bicyclic or tricyclic group selected from the group consisting of:

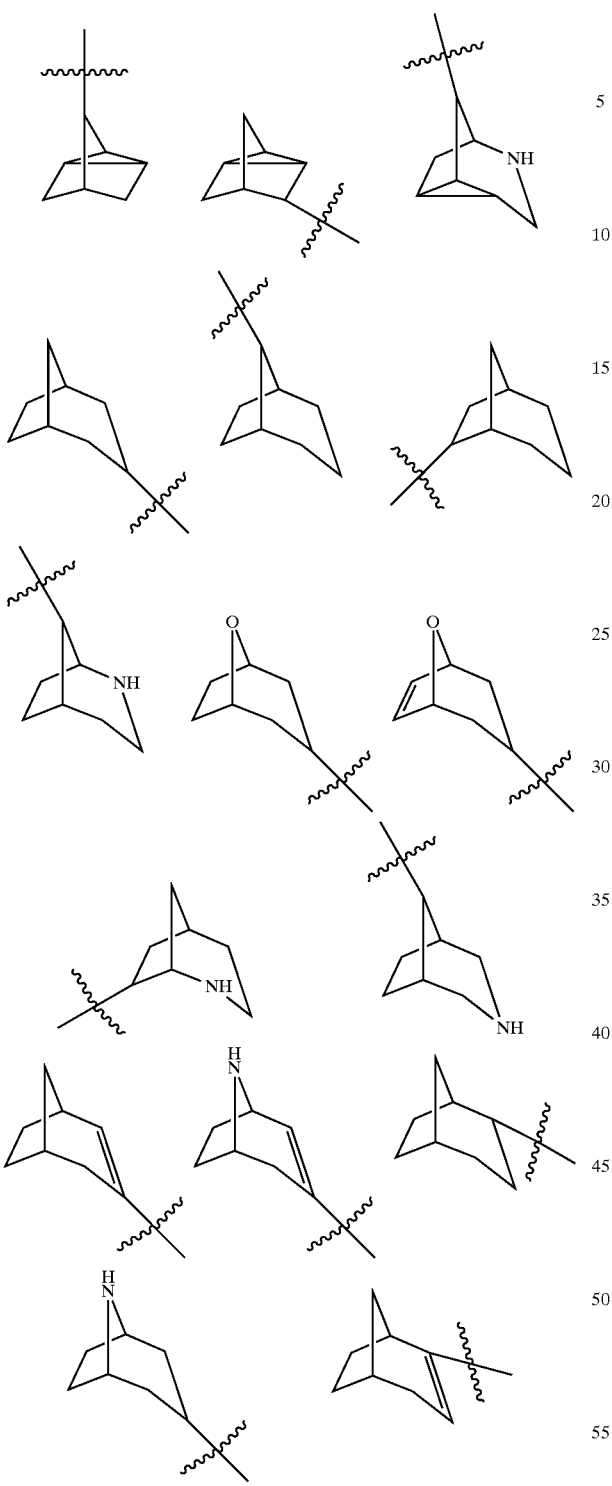

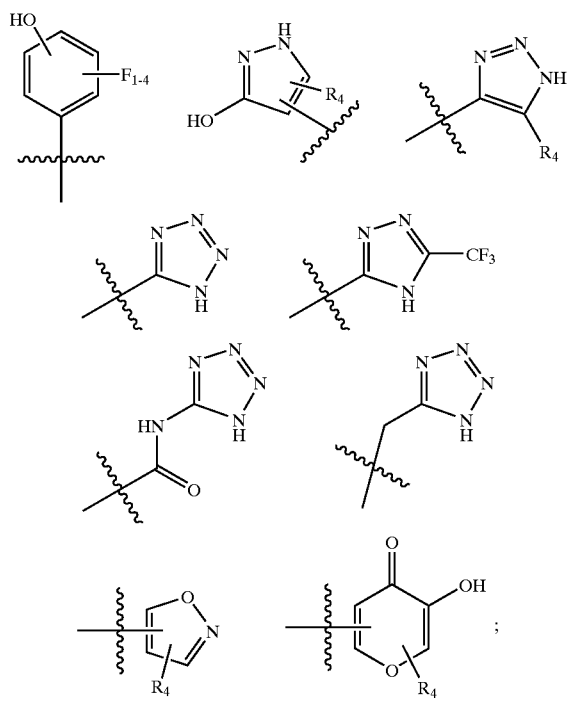

wherein the bicyclic or tricyclic group is either unsubstituted or substituted with one or more substituents selected from the group consisting of:

(a) alkyl, alkenyl, and alkynyl; wherein the alkyl, alkenyl, and alkynyl are either unsubstituted or substituted with one or more substituents selected from the group consisting of alkoxy, alkoxycarbonyl, alkoxycarbonylaminoalkylamino, aralkoxycarbonyl, —R5, dialkylamino, (heterocyclylalkyl)amino, hydroxy, substituted arylsulfonylaminoalkylamino, and substituted heterocyclylaminoalkylamino;

(b) acylaminoalkylamino, alkenylamino, alkoxycarbonyl, alkoxycarbonyl, alkoxycarbonylalkylamino, alkoxycarbonylaminoacyloxy, alkoxycarbonylaminoalkylamino, alkylamino, amino, aminoacyloxy, —$R_5$, $R_5$-alkoxy, dialkylaminoalkylamino, heterocyclyl, (heterocyclylalkyl)amino, hydroxy, substituted arylsulfonylaminoalkylamino, substituted heterocyclyl, and substituted heterocyclylaminoalkylamino;

$R_4$ is selected from the group consisting of —H, —$C_{1-4}$-alkyl, —$C_{1-4}$-alkyl-$CO_2H$, and phenyl; wherein said —$C_{1-4}$-alkyl, —$C_{1-4}$-alkyl-$CO_2H$, and phenyl are either unsubstituted or substituted with one or more substituents selected from the group consisting of halogen, —OH, —OMe, —$NH_2$, $NO_2$ or benzyl, optionally substituted with one to three groups selected from halogen, —OH, —OMe, —$NH_2$, and —$NO_2$;

$R_5$ is selected from the group consisting of —$CH_2COOH$, —$C(CF_3)_2OH$, —$CONHNHSO_2CF_3$, —$CONHOR_4$, —$CONHSO_2R_4$, —$CONHSO_2NHR_4$, —$C(OH)R_4PO_3H_2$, —$NHCOCF_3$, —$NHCONHSO_2R_4$, —$NHPO_3H_2$, —$NHSO_2R_4$, —$NHSO_2NHCOR_4$, —$OPO_3H_2$, —$OSO_3H$, —$PO(OH)R_4$, —$PO_3H_2$, —$SO_3H$, —$SO_2NHR_4$, —$SO_3NHCOR_4$, —$SO_3NHCONHCO_2R_4$, and:

$X_1$ and $X_2$ are independently selected from O and S;

Z is selected from the group consisting of a single bond, —O—, —$(CH_2)_{1-3}$—, —$O(CH_2)_{1-2}$—, —$CH_2OCH_2$—, —$(CH_2)_{1-2}O$—, —CH=$CHCH_2$—, —CH=CH—, and —$CH_2CH$=CH—; and $R_6$ is selected from the group consisting of hydrogen, alkyl, acyl, alkylsufonyl, aralkyl, substituted aralkyl, alkyl, and heterocyclyl.

2. The compound of claim 1, wherein $R_1$ and $R_2$ are each alkyl groups.

3. The compound of claim 1, wherein $R_1$ and $R_2$ are each n-propyl.

4. The compound of claim 3, wherein Z is a single bond.

5. The compound of claim 1, wherein $R_3$ is selected from the group consisting of:

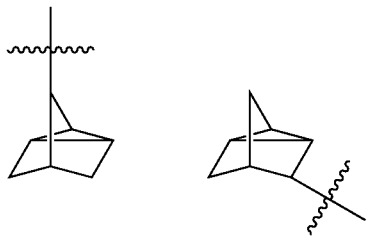

and is substituted with one or more substituents selected from hydroxy, alkenyl, alkenyloxy, hydroxyalkyl, carboxy, carboxyalkenlyl, carboxyalkyl, aminoacyloxy, carboxyalkoxy, dialkylaminoalkenyl, and dialkylaminoalkyl.

6. The compound of claim 1, wherein $R_3$ is:

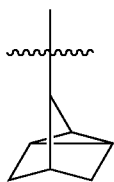

and is substituted with one or more substituents selected from hydroxy, alkenyl, carboxyalkenyl, hydroxyalkyl, dialkylaminoalkenyl, and dialkylaminoalkyl.

7. The compound of claim 6, wherein $R_3$ is substituted with a substituent selected from the group consisting of hydroxy, hydroxyalkyl, dialkylaminoalkenyl, and dialkylaminoalkyl.

8. The compound of claim 1, wherein the compound is 8-(5-Hydroxy-tricyclo[2.2.1.0$^{2,6}$]hept-3-yl)-1,3-dipropyl-3,7-dihydro-purine-2,6-dione.

9. The compound of claim 1, wherein the compound is 8-(5-Hydroxymethyl-tricyclo[2.2.1.0$^{2,6}$]hept-3-yl)-1,3-dipropyl-3,7-dihydro-purine-2,6-dione.

10. The compound of claim 1, wherein the compound is 8-[5-(3-Dimethylaminopropylidene)-tricyclo[2.2.1.0$^{2,6}$]hept-3-yl]-1,3-dipropyl-3,7-dihydro-purine-2,6-dione.

11. The compound of claim 1, wherein the compound is 8-[5-(3-Dimethylaminopropyl)-tricyclo[2.2.1.0$^{2,6}$]hept-3-yl]-1,3-dipropyl-3,7-dihydro-purine-2,6-dione.

12. The compound of claim 1, wherein $R_3$ is selected from

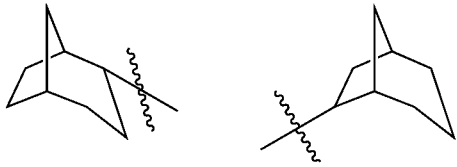

-continued

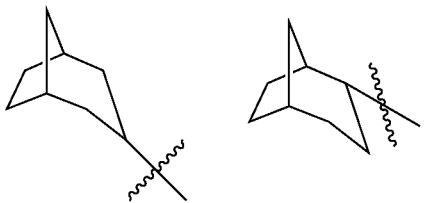

and is substituted with one or more substituents selected from the group consisting of hydroxy, alkyl, —$R_5$, $R_5$-alkyl, dialkylaminoalkylamino, alkoxycarbonylalkylamino, heterocyclyl, alkenylamino, amino, alkylamino, (heterocyclylalkyl)amino, acylaminoalkylamino, heterocyclylaminoalkylamino, and heterocyclylaminoalkylaminoalkyl.

13. The compound of claim 1, wherein $R_3$ is

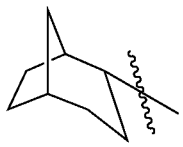

and is substituted with one or more substituents selected from the group consisting of hydroxy, —$R_5$, $R_5$-alkyl, and hydroxyalkyl.

14. The compound of claim 1, wherein the compound is 4-(2,6-Dioxo-1,3-dipropyl-2,3,6,7-tetrahydro-1H-purin-8-yl)-bicyclo[3.2.1]octane-1-carboxylic acid.

15. The compound of claim 1, wherein $R_3$ is:

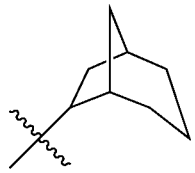

and is substituted with one or more substituents selected from the group consisting of alkyl, hydroxy, —$R_5$, and $R_5$-alkyl.

16. The compound of claim 1, wherein the compound is 8-(4-Hydroxy-bicyclo[3.2.1]oct-6-yl)-1,3-dipropyl-3,7-dihydro-purine-2,6-dione.

17. The compound of claim 1, wherein the compound is in a form selected from the group consisting of an achiral compound, a racemate, an optically active compound, a pure diastereomer, and a mixture of diastereomers.

18. The compound of claim 1, wherein $R_3$ is:

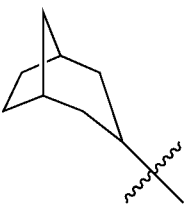

and is substituted with one or more substituents selected from the group consisting of hydroxy, dialkylaminoalkylamino, —R5, and substituted heterocyclylaminoalkylaminoalkyl.

19. The compound of claim 1, wherein the compound is 8-[8-(2-Dimethylaminoethylamino)-bicyclo[3.2.1]oct-3-yl]-1,3-dipropyl-3,7-dihydro-purine-2,6-dione.

20. The compound of claim 1, wherein the compound is 8-(8-Hydroxy-bicyclo[3.2.1]oct-3-yl)-1,3-dipropyl-3,7-dihydro-purine-2,6-dione.

21. The compound of claim 1, wherein $R_3$ is:

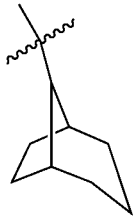

and is substituted with one or more substituents selected from the group consisting of hydroxy and —R5.

22. The compound of claim 1, wherein the compound is 8-(3-Hydroxy-bicyclo[3.2.1]oct-8-yl)-1,3-dipropyl-3,7-dihydro-purine-2,6-dione.

23. The compound of claim 5, wherein $R_3$ is selected from the group consisting of:

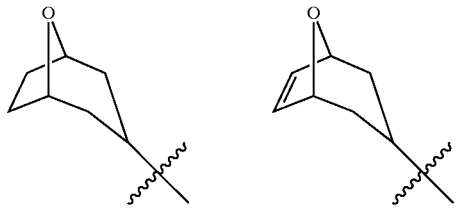

and is substituted with one or more substituents selected from the group consisting of hydroxyalkyl, hydroxy, and alkoxycarbonyl.

24. The compound of claim 1, wherein the compound is 8-(8-Oxa-bicyclo[3.2.1]oct-6-en-3-yl)-1,3-dipropyl-3,7-dihydro-purine-2,6-dione.

25. The compound of claim 1, wherein $R_3$ is:

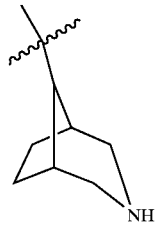

and is substituted with one or more substituents selected from the group consisting of aralkyloxycarbonylalkyl and alkoxycarbonylalkyl.

26. The compound of claim 1, wherein the compound is 8-(2-Oxo-3-aza-bicyclo[3.2.1]oct-8-yl)-1,3-dipropyl-3,7-dihydro-purine-2,6-dione.

27. A medicament composition comprising a compound of claim 1 together with a suitable excipient.

28. A method of treating a subject suffering from a disease selected from the group consisting of congestive heart failure and renal dysfunction, comprising administering to the subject an effective adenosine antagonizing amount of a compound of claim 1.

29. A method of treating a subject suffering from a disease selected from the group consisting of respiratory disorders, diseases for which diuretic treatment is indicated, depression, traumatic brain damage, respiratory depression, cystic fibrosis, cirrhotic ascites, neonatal apnea, renal failure, diabetes, and asthma, comprising administering to the subject an effective adenosine antagonizing amount of a compound of claim 1.

* * * * *